(12) United States Patent
Aubrecht et al.

(10) Patent No.: US 6,956,113 B2
(45) Date of Patent: Oct. 18, 2005

(54) BIOLUMINESCENT ASSAYS AND BACTERIAL STRAINS USEFUL THEREIN

(75) Inventors: Jiri Aubrecht, Mystic, CT (US); Warren W. Ku, West Kingstown, RI (US); Jeffery J. Osowski, Bozrah, CT (US)

(73) Assignee: Pfizer Inc., New York, NY (US)

( * ) Notice: Subject to any disclaimer, the term of this patent is extended or adjusted under 35 U.S.C. 154(b) by 19 days.

(21) Appl. No.: 10/029,741

(22) Filed: Dec. 21, 2001

(65) Prior Publication Data

US 2002/0192635 A1 Dec. 19, 2002

Related U.S. Application Data

(60) Provisional application No. 60/258,073, filed on Dec. 22, 2000.

(51) Int. Cl.⁷ .............................................. C07H 21/04

(52) U.S. Cl. ................. 536/23.1; 435/172.3; 435/172.2; 435/235.1; 536/23.4

(58) Field of Search ........................... 435/172.3, 172.2, 435/235.1, 70.2, 44.1, 44.9; 536/23.1, 23.4

(56) References Cited

FOREIGN PATENT DOCUMENTS

| WO | WO 9303179 | 2/1993 | ............ C12Q/1/66 |
|----|------------|--------|------------------------|
| WO | WO 9413831 | 6/1994 | ............ C12Q/1/68 |
| WO | WO 94/13831 | * 8/1994 | |
| WO | WO 9616187 | 5/1996 | ............ C12Q/1/68 |
| WO | WO 9821347 | 5/1998 | ............ C12N/15/70 |

OTHER PUBLICATIONS

Ames, B.N. et al., "Carcinogens are mutagens: a simple test system combining liver homogenates for activation and bacteria for detection," *Proc. Natl. Acad. Sci. USA* 70: 2281–2285 (1973a)(co–incubation of a carcinogen, a rat or human liver homogenate, and the bacterial tester strain on a petri plate).

Ames, B.N. et al., Methods for detecting carcinogens and mutagens with *Salmonella*/mammalian–microsome mutagenicity test, *Mutation Res.* 31: 347–364 (1975).

Brooks, T.M., "The use of a streamlined bacterial mutagenicity assay, the MINISCREEN," *Mutagenesis* 10(5): 447–448 (1995).

de Lorenzo, V., et al., "Mini–Tn5 transposon derivatives for insertion mutagenesis, promoter probing, and chromosomal insertion of cloned DNA in gram–negative eubacteria," *J. Bacteriol.* 172(11): 6568–65 (1990).

Falck, K., et al., "Mutascreen®, an automated bacterial mutagenicity assay," *Mutation Res.* 150: 119–125 (1985).

Gee, P. et al., "Detection and classification of mutagens: A base set of base–specific *Salmonella* tester strains," *Proc. Natl. Acad. Sci. USA* 91: 11606–11610 (1994).

Green, M.H.L. & Muriel, W.J., "Mutagen testing using Trp reversion in *Escherichia coli*," *Mutation Res.* 38: 3–32 (1976).

Haworth, S., et al., "*Salmonella* mutagenicity results for 250 chemicals," *Environ. Mutagen.* 5(Suppl. 1): 3–142 (1983).

Houk, V.S. et al., "Development and validation of the spiral *Salmonella* assay: An automated approach to bacterial mutagenicity testing," *Mutation Res.* 223: 49–64 (1989)(dose–response data is generated from a continuous concentration gradient on a single agar plate).

Johnston, T.C. et al., "The nucleotide sequence of the luxA and luxB genes of *Xenorhabdus luminescens* HM and a comparison of the amino acid sequences of luciferases from four species of bioluminescent bacteria," *BBRC* 170: 407–415 (1990).

Kado, N.Y. et al., "A simple modification of the *Salmonella* liquid incubation assay: increased sensitivity for detecting mutagens in human urine," *Mutat. Res.* 112:25–32 (1983).

Marincs, F. & White, D.W.R., "Immobilization of *Escherichia coli* Expressing the lux Genes of *Xenorhabdus luminescens*," *Appl. Environ. Microbiol.* 60(10): 3862–3863 (1994).

Maron, D.M. and Ames, B.N., "Revised methods for the *Salmonella* mutagenicity test," *Mutation Res.* 113: 173–215 (1983).

McCann, J. et al., "Detection of carcinogens as mutagens: bacterial tester strains with R factor plasmids," *Proc. Natl. Acad. Sci. USA* 72(3): 979–983 (1975).

McPherson, M.F. and Nestmann, E.R., "The SIMULTEST approach for testing mutagens in the *Salmonella* microtitre fluctuation assay," *Environ. Mol. Mutagen.* 16: 21–25 (1990).

Skulachev, V.P., "The sodium cycle: a novel type of bacterial energetics,"*J. Bioenerg. Biomembr.* 21(6): 635–647 (1989).

Szittner, R. & Meighen, "Nucleotide sequence, expression and properties of luciferase coded by lux genes from a terrestrial bacterium," *JBC* 265: 16581–16587 (1990).

Voisey, C.R. & Marincs, F., "Elimination of Internal Restriction Enzyme Sites from a Bacterial Luminescence(luxCD-ABE) Operon," *Bio Techniques* 24:56–58 (1998).

(Continued)

*Primary Examiner*—T. D. Wessendorf
(74) *Attorney, Agent, or Firm*—Peter C. Richardson; Gregg C. Benson; Gabriel L. Kleiman

(57) ABSTRACT

The present invention relates to novel assays for assessing the degree to which a cell is metabolically active. Also provided, are mutagenicity assays and, more specifically, methods for determining whether a given agent is genotoxic. Embodiments of the assays employ a microorganism, or a mammalian cell, that has been genetically modified to produce light when the presence of test agent results in a mutation, e.g., reversion or forward, in the DNA of such microorganism or cell.

2 Claims, 8 Drawing Sheets

OTHER PUBLICATIONS

Walker, G.C., "Plasmid (pkM101)–mediated enhancement of repair and mutagenesis: dependence on chromosomal genes in *Escherichia coli* K–12," *Mol. Gen. Gent.* 152(1): 93–103 (1977).

Xi, L. et al., "Cloning and nucleotide sequences of lux genes and characterization of luciferase of *Xenorhabdus luminescens* from a human wound," *J. Bacteriol.* 173: 1399–1405 (1991).

C. Côte et al., Mutation Research, 1995, vol. 345, pp 137–146, "A miniaturized Ames mutagenicity assay employing bioluminescent strains of *Salmonella* typhimurium".

P. Billard et al., Clinical Biochemistry, 1998, vol. 31, pp 1–14, "Bioluminescence–based assays for detection and characterization of bacteria and chemicals in clinical laborators".

* cited by examiner

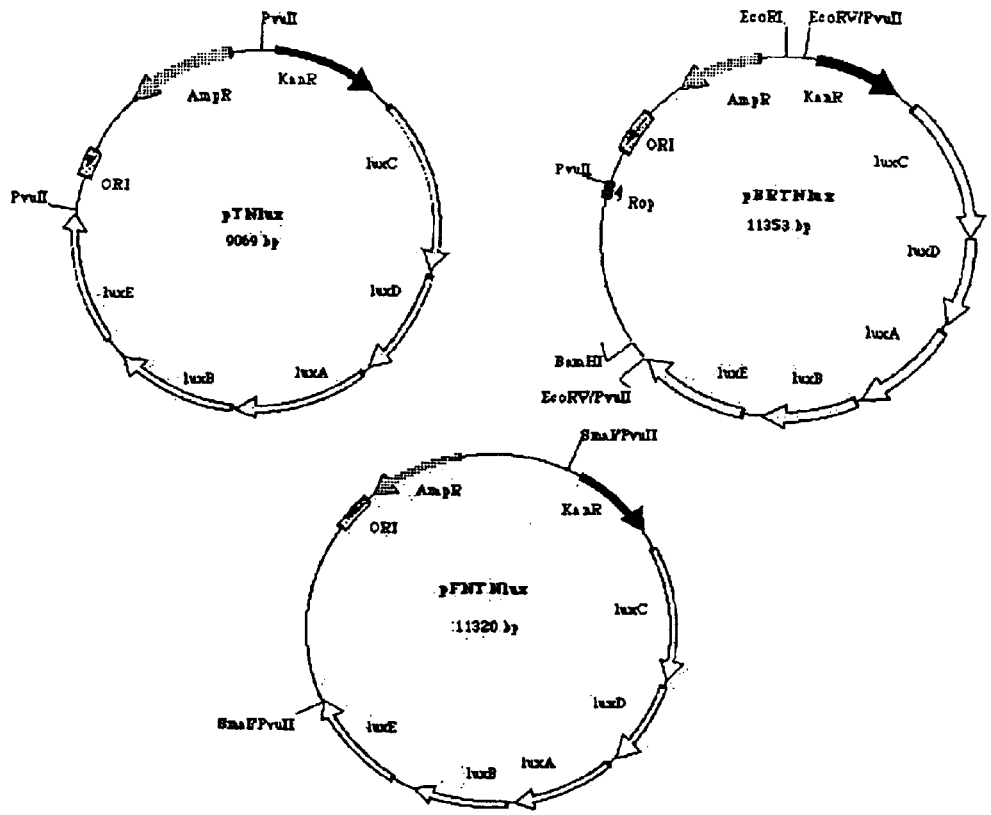

Figure 1. Plasmids used for the development of bacterial tester strains for embodiments of the bioluminescent "Ames" assays of the present invention. The plasmid pTNlux is a high copy vector based on pUC19 backbone. It was used as a source of the lux(CDABE) expression cassette (PvuII fragment). The plasmid pBRTNlux is a medium copy plasmid based on pBR322 backbone. The plasmid pFNTNlux is a low copy vector based on pFN476 backbone. AmpR, β-lactamase (ampicillin resistance); KanR, kanamycin resistance gene; ORI, origin of replication; Rop, rop gene. SmaI/PvuII and EcoRV/PvuII indicate ligation of PvuII end into SmaI or EcoRI site, respectively.

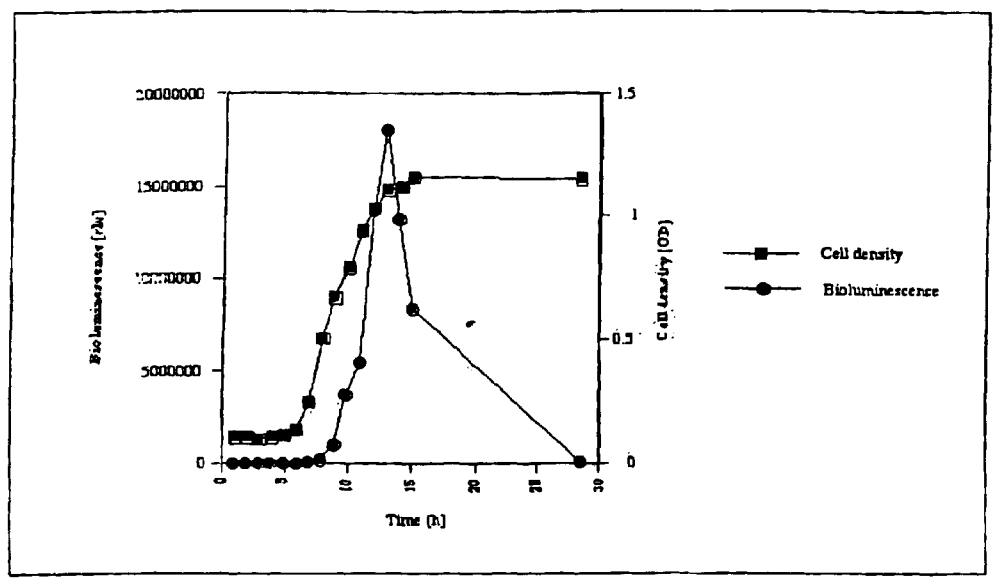
Figure 2. Levels of bioluminescence emitted by bacteria, prepared according to the present invention, during growth phases of bacterial culture. The values shown represent the average of three independent determinations.

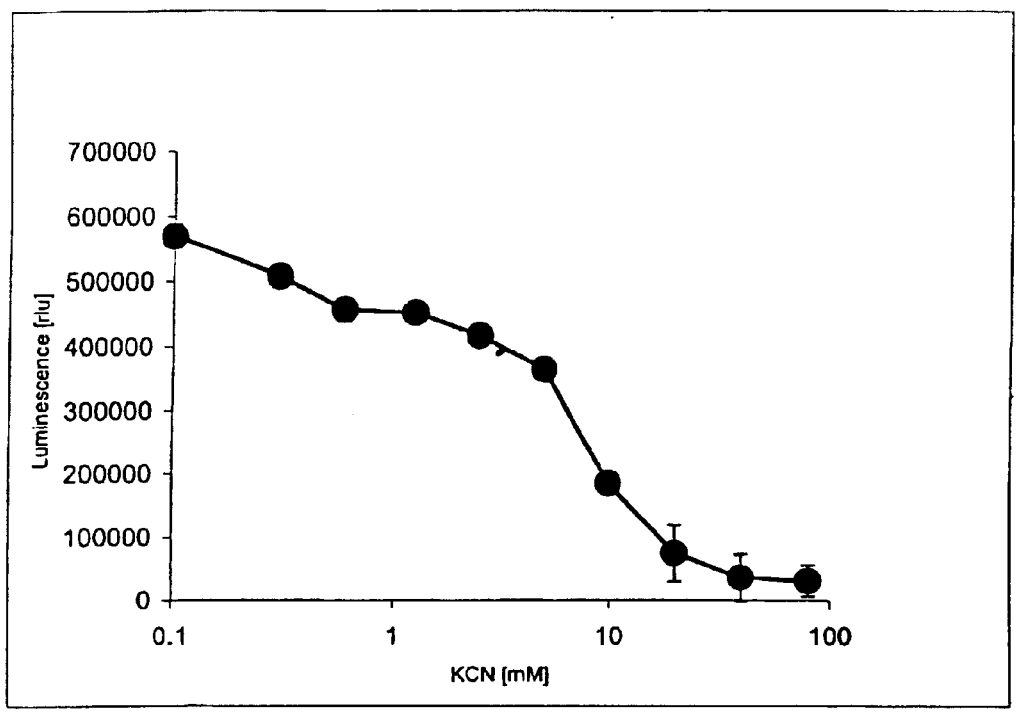
Figure 3. Influence of KCN on bioluminescence. The cells, prepared as provided by the present invention, were exposed to increasing concentrations of KCN. The bioluminescence was measured immediately after the addition of KCN. The values represent averages ± SD.

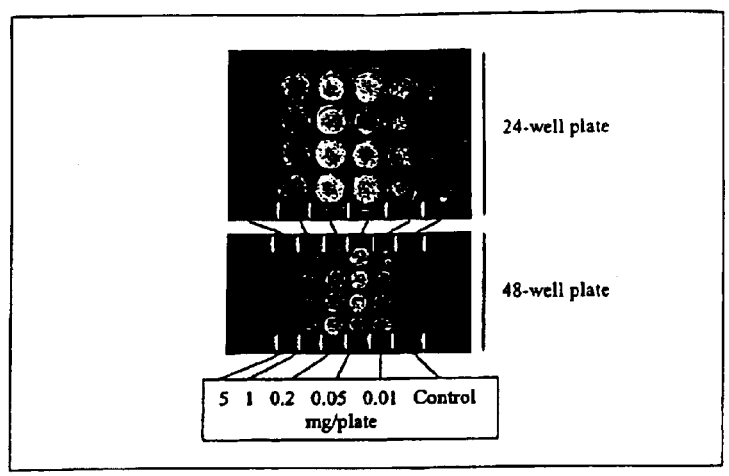

Figure 4. Bioluminescent detection of revertants of the present invention after treatment with the model mutagen MNNG. Images of bioluminescent microcolonies of revertants prepared according to the assays of the present invention. Results of assays, in quadruplicate, are shown; the concentrations of MNNG (mg/plate) reflect the standard (pour plate) Ames Assay.

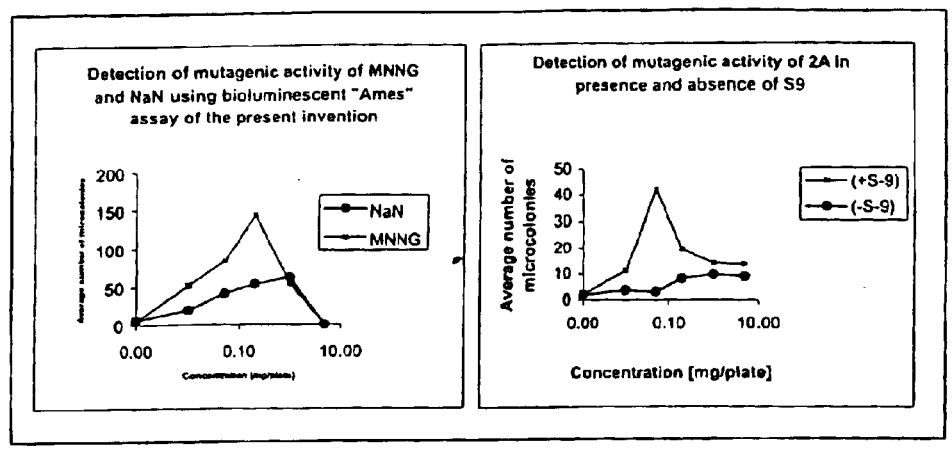
Figure 5. Detection of model mutagens using bioluminescent "Ames" assays of the present invention. The values represent an average number of revertant microcolonies from quadruple determinations.

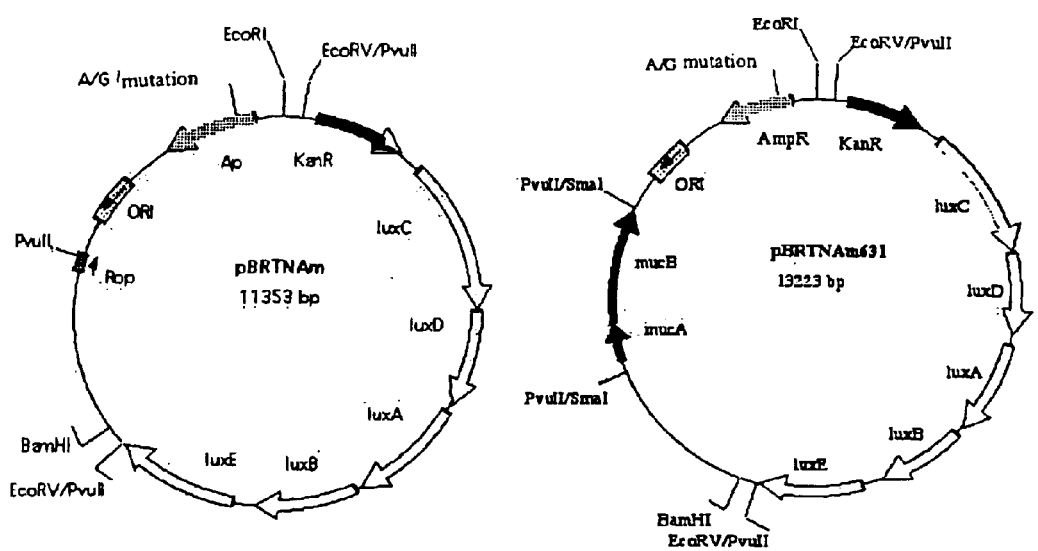

Figure 6. Plasmids used for the development of bacterial tester strains for embodiments of the bioluminescent β-lactamase assays of the present invention. Plasmid pBRTNAm and pBRTNAm631 are based on pBR322 backbone. AmpR, β-lactamase (ampicillin resistance); KanR, kanamycin resistance gene; ORI, origin of replication; PvuII/SmaI and EcoRV/PvuII indicate ligation blunt ended DNA fragments that cannot be recleaved.

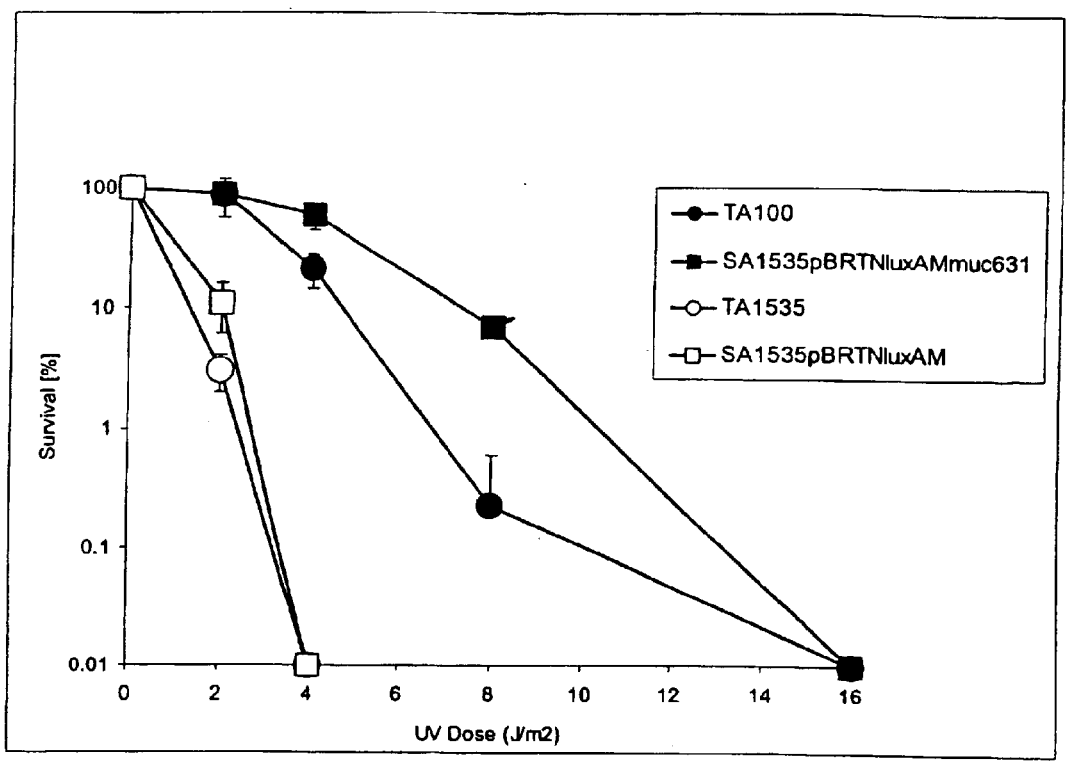
Figure 7. Influence of mucAB expression on UV sensitivity of *Salmonella typhimurium*. Bacterial cells, prepared according to the present invention, were exposed to increasing levels of UV light. The surviving cells were detected after incubation on LB plates. The values represent averages ± SD.

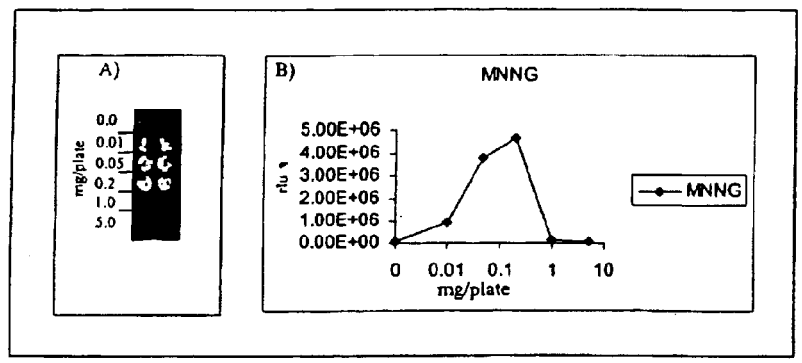

Figure 8. Detection of mutagenic activity of a known mutagen MNNG using an embodiment of the bioluminescent β-lactamase assays of the present invention. The assay was performed, as provided by the present invention, in 96 well plates, and the bioluminescence emitted was measured using a photon-counting camera. A) Image of treated wells; B) dose-response curve; the concentrations of MNNG (mg/plate) reflect the standard (pour plate) Ames Assay.

BIOLUMINESCENT ASSAYS AND BACTERIAL STRAINS USEFUL THEREIN

CROSSREFERENCE TO RELATED APPLICATION

This application claims priority from U.S. Provisional Patent Application No. 60/258,073 filed Dec. 22, 2000, the benefit of which is hereby claimed under 37 C.F.R. §1.78 (a)(3).

FIELD OF THE INVENTION

The present invention relates to novel bioluminescent assays, and to bacterial strains useful therein. More specifically, these assays enable one to distinguish metabolically active cells from non-metabolically active cells. In a particularly preferred embodiment, these assays enable one to ascertain whether a given test agent is a genotoxin, or mutagen.

BACKGROUND OF THE INVENTION

Fundamental to pharmaceutical research and development is an early determination of whether a particular proposed agent presents a hazard of mutagenicity, or genotoxicity. It is generally accepted that the mutagenic potential of a particular agent, e.g., compound, is roughly proportional to its carcinogenic potential.

Mutagens are agents, such as chemical carcinogens, that cause an increase in the rate of mutation. A mutation is generally thought of as a change in the DNA sequence of an organism due to, e.g., gene or point mutations, primary DNA damage and repair, or chromosomal alterations.

Commonly employed tests for detecting mutagens or genotoxins (mutagenicity tests) include, for example, the *Salmonella* mutagenicity test (Ames Test, Ames et al., 1973a, 1973b, and 1975; see also, Ames, B. N., 1971), and the more recent *Salmonella* or *Escherichia coli* lactam mutagenicity tests (β-lac tests, Lee, C -C, et al., 1994, and Hour, T -C., et al., 1995). Both of these tests are based on the ability of DNA damaging agents to produce reverse mutations in certain bacterial genes. The *Salmonella* mutagenicity test uses *Salmonella* strains that each contain a different type of mutation in the his (histidine biosynthesis) operon, e.g., frameshift or base pair substitutions. The *Salmonella* or *Escherichia coli* (*E. col*) strains used in the lactam mutagenicity test contain a plasmid which itself contains a β-lactamase gene site having a mutation precluding β-lactamase expression. The β-lactamase gene encodes a protein that hydrolyses amide bonds in β-lactam rings of penicillins and Cephalosporins to derivatives devoid of antimicrobial activity, thus rendering such microbes able to resist antibiotics of the β-lactam class.

This *Salmonella* test system, also known as the *Salmonella/mammalian* microsome mutagenicity assay, allows for the screening of suspected carcinogens, the isolation of carcinogens from natural materials, and the identification of the active forms of carcinogens. The Ames Test, the most widely used and investigated mutagenicity assay (see, for example, Maron, D. M. and Ames, B. N., 1983; Dunkel, V. C. et al., 1985; and Zeiger, E., 1985; and Kier, L. E. et al., 1986), remains the recommended assay for bacterial mutagenesis.

Variations of the *Salmonella/mammalian* microsome mutagenicity assay continue to be reported by Ames and others (see, for example, Yahagi, T. et al., 1975; Prival, M. J. and Mitchell, V. D. 1982; Haworth, S. et al., 1983; Kado, N. Y., et al., 1983; and Reid, T. M., et al., 1984; and *Current Protocols in Toxicology*, John Wiley & Sons, Inc. (2000), Chapter 3. Genetic Toxicology: Mutagenesis and Adduct Formation, Chapter 3 Introduction, Unit 3.1 The *Salmonella* (Ames) Test for Mutagenicity, Alternate Protocol 1: Plate Assay With Preincubation Procedure; Alternate Protocol 2: Desiccator Assay for Volatile Liquids; Alternate Protocol 3: Desiccator Assay for Gases; Alternate Protocol 4: Reductive Metabolism Assay; Alternate Protocol 5: Modified (Kado) Microsuspension Assay).

Several of these modifications have generally focused on minimizing the required amount of test agent and increasing throughput, i.e., minimizing the manual work of the Ames Test (standard plate-incorporation whereby the bacterial tester strain is exposed to incremental doses of the test agent in the presence of an exogenous metabolic activation system) (see, for example, Waleh, N. S. et al., 1982; and *Current Protocols in Toxicology*, Chapter 3. Genetic Toxicology: Mutagenesis and Adduct Formation, Chapter 3 Introduction, Unit 3.1 The *Salmonella* (Ames) Test for Mutagenicity, Support Protocol 1: Toxicity Test for Dose Selection).

A revised protocol (preincubation assay) that deviates from Ames' standard agar plate incorporation has been described (Maron, D. M. and Ames, B. N., 1983). Another variation, Mutascreen®, combines turbidimetric and kinetic principles into a bacterial mutagenicity test based on the same biological system as in the Ames Test (Falck, K., et al., 1985).

The spiral *Salmonella* assay, another automated approach to bacterial mutagenicity testing, reportedly eliminates the need for serial dilutions and multiple plates to obtain the dose-response data (see, for example, DeFlora, S., 1981; Couse, N. L. & King, J. W., 1982; Houk, V. S. et al., 1989, and 1991).

Other methods retain the use of solid agar plating, such as, for example, the automated liquid preincubation exposure protocol described by Kato, H. et al., 1995.

The Miniscreen, a scaled-down version of the Ames Test, describes the use of smaller quantities of test agent (20 mg) versus the 2 g of test agent reportedly required by the Ames test, and is used as a blanket or pre-screen for various types of test agents (Brooks, T. M., 1995; see also, Burke, D. A. et al., 1996).

Further, the Ames II™ test (Xenometrix) is described as a modification to the fluctuation assay (Green, M. H. L. et al., 1976; Gatehouse, D. G. & Delow, G. F., 1979; and McPherson, M. F. & Nestmann, E. R., 1990) to allow automation of plating the exposed cells in selective media using the TA7000 series of tester strains.

Despite the relatively continued provision to the art of such modified protocols, for example, as provided above, the Ames Test remains the recommended assay for bacterial mutagenesis; hence, those skilled in the art will appreciate that there remains a need for assays that further overcome the limitations of the original and modified versions of the assay, such as, for example, the amount of test agent required, the amount of time it takes to reach a result, manual counting of revertant colonies, the lack of ease of scalability to high throughput assays, and the like.

Likewise, those skilled in the art will understand that similar limitations exist in relation to the known β-lactam tests, which measure reverse mutation from ampicillin-sensitivity to ampicillin-resistance (see, for example, Bosworth, D. et al., 1987; Foster, P. L. et al., 1987; Delaire, M. et al., 1991; Lee, C -C., et al., 1994; and Hour, T -C., et al., 1998), as well as the known mutagenicity assay premised on the point mutation in a tryptophan gene (e.g., using *E. coli* WP2, see, for example, McCalla, D. R. and Voutsinos, D., 1974).

The present invention provides, in part, improved reverse mutagenicity assays. The assays preferably employ the well characterized *Salmonella typhimurium* strains utilized in the Ames Test, except that these strains have been further modified as described herein to contain a plasmid comprising an expressible heterologous lux(CDABE) gene complex under the control of a constitutive promoter. This is to empower these microorganisms to emit light as a readout when metabolically active as described in more detail hereinbelow.

Bacterial bioluminescence and lux operons, as well as applications thereof, are well known in the art (see, for example, Meighen, E. A., 1988; Frackman, S. et al., 1990; Jassim, S. A. A. et al., 1990; Stewart, G. S. A. B., 1990; Stewart, G. S. A. B. & Williams, P., 1992; Meighen, E. A., 1993; Hill, P. J., et al., 1993; Bronstein, I. et al., 1994; Hill, P. J. & Stewart, G. S. A. B, 1994; Marincs, F. & White, D. W. R., 1994; Chatterjee, J. & Meighen, E. A., 1995; and Voisey, C. R. & Marincs, F., 1998).

The luxA and luxB genes of the lux structural operon encode the non-identical α and β subunits of a bacterial luciferase, respectively, and are widely used as reporter genes (see, for example, Stewart, G. S. A. B. & Williams, P., 1992; and Chatterjee, J. & Meighen, E. A., 1995). The resultant heterodimer catalyzes the oxidation of $FMNH_2$ and a long-chain fatty aldehyde, which results in an emission of light. Metabolically active bacterial cells produce $FMNH_2$.

The luxC, luxD, and luxE genes of the lux operon encode the fatty reductase complex, where luxC encodes the reductase polypeptide, luxD encodes the transferase polypeptide, and luxE encodes the synthetase polypeptide. The fatty acid reductase complex produces the aldehyde substrate necessary for the luciferase. The cleavage of the substrate by the luciferase requires endogenous $FMNH_2$ and produces bioluminescence.

The bacterial bioluminescence reaction also requires endogenous $FMNH_2$ and $O_2$. As described above, metabolically active bacterial cells produce $FMNH_2$. Metabolically active cells of the novel bacterial tester strains will be those that, after exposure to a test agent, revert to a non-mutant phenotype, and thus are able to grow in a selective medium, e.g., a medium not containing histidine, a medium not comprising tryptophan, a medium comprising ampicillin, as the case may be, and due to such growth (or metabolic activity) emit luminescence, in an amount greater than the amount, if any, produced by the degree of spontaneous reversion of the mutation, where the degree of spontaneous reversion can be measured, for example, by having additional samples in a given assay that contain, e.g., vehicle (e.g., solvent) and cell only, and/or vehicle and cell and exogenous metabolic activation system. Further, where so desired, the presence of the test agent can be in the presence and absence of the exogenous metabolic activation system.

Depending upon the novel bacterial strain selected, as little as ng/µg amounts of a test agent may be used. In addition, the bioluminescence readout of light-producing revertant colonies is substantially immediate, and due to the constitutive promoter driving the lux(CDABE) expression, maintained as long as the revertant colonies maintain their metabolic activities, e.g., produce $FMNH_2$. Thus, the present invention provides assays that utilize bioluminescence as a sensor for a cell's ability to produce energy. Hence, the present assays can be adapted, based on the present description, as so desired, to any assay using metabolic activity as a readout.

Moreover, the cell for use in the assays of the present invention can be a mammalian cell, which contain a variety of luciferases (see, for example, Bronstein, I., et al., 1994). The most common is luc gene from American firefly (*Photinus pyralis*). In this system, luciferin serves as substrate for cleavage by the luciferase encoded by the luc gene. Hence, an exogenous substrate, e.g., a luciferin, is supplied, in any suitable manner, to the assays of this invention that utilize mammalian cells. Further, the bioluminescent reaction requires ATP, as source of energy, and oxygen which, as those skilled in the art will appreciate, is abundant in the environment.

The improvements to the Ames Test, and to the modifications thereof, provided by the present invention, further decrease the amount of test agent required and the laboriousness of such protocols, and enable a substantially immediate readout, and thus a determination of whether a particular test agent causes a reversion of a point mutation, i.e., is a mutagen. Such assays readily allow for automation and scale-up for the long sought after assay capability for high throughput screening. Such scalability provides substantial utility to the pharmaceutical industry by enabling high throughput screening of putative pharmaceutical products (for mutagenicity or genotoxicity) at the very early stages of pre-clinical research. The early read on genotoxicity can decrease the aftrition of pharmaceutical product candidates, thus enhancing the efficiency of decision making. Moreover, the assays provided by the present invention can also be used to determine the characteristics, e.g., particular substituents, of compounds that confer genotoxicity to the compound and, as such, assist in the design of non-mutagenic compounds.

All of the documents cited herein, including the foregoing, are incorporated by reference herein in their entireties.

SUMMARY OF THE INVENTION

The present invention provides, in a first aspect, novel assays for assessing the extent to which a cell is metabolically active, comprising: measuring an amount of light emitted by a cell comprising an expressible heterologous lux(CDABE) gene complex under the control of a constitutive promoter; changing the environment of said cell; and comparing the amount of light emitted by said cell prior to said change with the amount of light emitted by said cell after said change; where an increase in said amount of said light emitted after said change means that said cell is more metabolically active after said change; and where a decrease in said amount of said light emitted after said change means that said cell is less metabolically active after said change; provided that said cell produces an amount of $FMNH_2$ sufficient for the light producing reaction when said cell is metabolically active.

In a preferred embodiment of the first aspect, the lux (CDABE) gene complex (or operon) is isolated from *Xenorhabdus luminescens*.

In another preferred embodiment of the first aspect, the cell is in a medium, and said change comprises the addition of a test agent to said medium.

In another preferred embodiment of the first aspect, the cell is in a medium, said change comprises the addition of a test agent to said medium, and said medium further comprises an exogenous metabolic activation system for said test agent.

In another preferred embodiment of the first aspect, the cell is in a medium, said change comprises the addition of a test agent to said medium, said medium further comprises an exogenous metabolic activation system for said test agent, and said cell is selected from the group consisting of *Salmonella typhimurium* TA1535lux (UC25447), *Salmonella typhimurium* TA100lux (UC25448), *Salmonella typhimurium* TA98lux (UC25449), said medium is substantially histidine-free, said exogenous metabolic activation system is an S-9 preparation, and said increase after said addition of said test means that said test agent reversed the histidine gene mutation of said cell.

In another preferred embodiment of the first aspect, the cell is in a medium, said change comprises the addition of a test agent to said medium, said medium further comprises an exogenous metabolic activation system for said test agent, and said cell is *E. coli* WP2lux (UC25452), said medium is substantially tryptophan-free, said exogenous metabolic activation system is an S-9 preparation, and said increase after said addition of said test means that said test agent reversed the tryptophan gene mutation of said cell.

In another preferred embodiment of the first aspect, the cell is in a medium, said change comprises the addition of a test agent to said medium, said medium further comprises an exogenous metabolic activation system for said test agent, and said cell is *Salmonella typhimurium* TA2220lux (UC25450) or *Salmonella typhimurium* TA2211lux (UC25451), said medium comprises ampicillin, said exogenous metabolic activation system is an S-9 preparation, and said increase after said addition of said test agent means that said test agent reversed the β-lactamase gene mutation of said cell.

In another preferred embodiment of said first aspect, the cell is in medium and said medium comprises more than one test agent.

In another preferred embodiment of said first aspect, the cell is in medium, said test agent is added to said medium, said test agent is a mutagen, and after said increase in said emitted light, another test agent is added to determine whether that second test agent causes the reversed mutation to revert to the mutant phenotype.

The present invention provides, in a second aspect, a cell comprising an expressible heterologous lux(CDABE) gene complex and a substantially reversible point mutation.

In a preferred embodiment of said second aspect, said point mutation is in a histidine gene.

In another preferred embodiment of said second aspect, said point mutation is in a histidine gene, and said cell is selected from the group consisting of: *Salmonella typhimurium* TA1535lux (UC25447), *Salmonella typhimurium* TA100lux (UC25448), and *Salmonella typhimurium* TA98lux (UC25449).

In another preferred embodiment of said second aspect, said point mutation is in a tryptophan gene.

In another preferred embodiment of said second aspect, said point mutation is in a tryptophan gene, and said cell is *Escherichia coli* WP2lux (UC25452).

In another preferred embodiment of said second aspect, said point mutation is in a β-lactamase gene.

In another preferred embodiment of said second aspect, said point mutation is in a β-lactamase gene, and said β-lactamase is in the active site serine codon.

In another preferred embodiment of said second aspect, said point mutation is in a β-lactamase gene, said β-lactamase is in the active site serine codon, and said cell is selected from *Salmonella typhimurium* TA2220lux (UC25450) and *Salmonella typhimurium* TA2211lux (UC25451).

Accordingly, the present invention provides bioluminescent reverse mutagenicity assays, which comprise: contacting a bacterial cell with an amount of a test agent and an amount of an exogenous metabolic activation system, where said cell comprises an expressible heterologous lux (CDABE) gene complex (or operon) and a reversible point mutation in a gene which in a non-mutated form encodes a polypeptide whose functioning is critical for the cell to be metabolically active in a selective medium; measuring an amount of light emitted from said cell; and comparing said amount of said light emitted by said cell exposed to said test agent and said exogenous metabolic activation system with substantially the same cell contacted with an exogenous metabolic activation system in the absence of said test agent; where an amount of emitted light is detected in said cell contacted with said test agent and said exogenous metabolic activation system, and substantially no amount of emitted light is detected in said cell exposed to said exogenous metabolic activation system in the absence of said test agent, means that said test agent is a mutagen; provided that, said cell produces an amount of $FMNH_2$ sufficient for the light producing reaction when said cell is metabolically active.

Any suitable material can be used as the test agent in an embodiment of the present invention. Preferred test agents include small molecules, peptides, any known or suspected mutagens and carcinogens, antibodies, antisense RNA, known inhibitors of metabolic activity, and the like. Particularly preferred test agents include small molecules, and known mutagens and carcinogens.

The present invention also provides, in a third aspect, novel assays for assessing the extent to which a cell is metabolically active, comprising: measuring an amount of light emitted by a cell comprising an expressible heterologous luc gene under the control of a constitutive promoter, in the presence of an amount of a luciferin; changing the environment of said cell; and comparing the amount of light emitted by said cell prior to said change with the amount of light emitted by said cell after said change; where an increase in said amount of said light emitted after said change means that said cell is more metabolically active after said change; and where a decrease in said amount of said light emitted after said change means that said cell is less metabolically active after said change; provided that said cell produces an amount of ATP sufficient for the light producing reaction when said cell is metabolically active.

In a preferred embodiment of the third aspect, the cell is in a medium, and said change comprises the addition of a test agent to said medium.

In another preferred embodiment of the third aspect, the cell is in a medium, said change comprises the addition of a test agent to said medium, and said medium further comprises an exogenous metabolic activation system for said test agent.

In another preferred embodiment of the third aspect, the cell is in a medium, said change comprises the addition of a test agent to said medium, said medium further comprises an exogenous metabolic activation system for said test agent, and said cell also comprises a reversible point mutation in a gene where a non-mutated gene provides a component critical for functioning of said cell in a selective medium.

In another preferred embodiment of the third aspect, the cell is in a medium, said change comprises the addition of a test agent to said medium, said medium further comprises an exogenous metabolic activation system for said test agent, and said cell also comprises a reversible point mutation in a gene where a non-mutated gene provides a component critical for functioning of said cell in a selective medium, wherein said medium is substantially free of said critical component provided by said non-mutated gene, said exogenous metabolic activation system is an S-9 preparation, and said increase after said addition of said test agent means that said test agent reversed the point mutation in said gene of said cell.

In another preferred embodiment of the third aspect, said cell also comprises a reversible point mutation in a gene, where a non-mutated form of said gene encodes a polypeptide critical for functioning of said cell in a selective medium.

The present invention also provides, in a fourth aspect, methods for determining characteristics (e.g., chemical and/ or structural) of a compound that confer mutagenicity to said compound, which comprise: contacting substantially identical bacterial cells with an amount of each compound of a compound library and an amount of an exogenous metabolic activation system substantially sufficient to activate said compound, where said cells each comprise an expressible heterologous lux(CDABE) gene complex (or operon) and a reversible point mutation in a gene which in a non-mutated form encodes a polypeptide whose functioning is critical for the cell to be metabolically active in a selective medium; measuring an amount of light emitted from each of said cells; and comparing said amount of said light emitted by each of said cells exposed to said amount of said compound of said compound library and said exogenous metabolic activation system with substantially the same cell contacted with an exogenous metabolic activation system in the absence of said amount of said compound of said compound library; where an amount of emitted light is detected in said cell contacted with said amount of said compound of said compound library and said exogenous metabolic activation system, and substantially no amount of emitted light is detected in said cell exposed to said exogenous metabolic activation system in the absence of said amount of a compound of said compound library, means that said compound of said compound library is a mutagen; and comparing the chemical and structural characteristics of each of said compounds of said library that caused light to be emitted to identify common characteristics; provided that, said cell produces an amount of $FMNH_2$ sufficient for the light producing reaction when said cell is metabolically active.

The present invention also provides, in a fifth aspect, methods for determining characteristics (e.g., chemical and/ or structural) of a compound that confer mutagenicity to said compound, which comprise: contacting substantially identical mammalian cells with an amount of each compound of a compound library, and an amount of an exogenous metabolic activation system substantially sufficient to activate said compound, where said cells each comprise an expressible heterologous luc gene and a reversible point mutation in a gene which in a non-mutated form encodes a polypeptide whose functioning is critical for the cell to be metabolically active in a selective medium, in the presence of a substrate for said polypeptide; measuring an amount of light emitted from each of said cells; and comparing said amount of said light emitted by each of said cells exposed to said amount of said compound of said compound library and said exogenous metabolic activation system with substantially the same cell contacted with an exogenous metabolic activation system in the absence of said amount of said compound library; where an amount of emitted light is detected in said cell contacted with said amount of said compound of said compound library and said exogenous metabolic activation system, and substantially no amount of emitted light is detected in said cell exposed to said exogenous metabolic activation system in the absence of said amount of a compound of said compound library, means that said compound of said compound library is a mutagen; and comparing the chemical and structural characteristics of each of said compounds of said library that caused light to be emitted to identify common characteristics; provided that, said cell produces an amount of ATP sufficient for the light producing reaction when said cell is metabolically active.

The test agent can also be a preparation containing more than one agent and, thus, the assays of the present invention can also be used to isolate a mutagenic test agent from non-mutagenic or less mutagenic components of the preparation. In addition, by activating the test agent using different methods to generate different metabolites, the mutagenic metabolite(s) can be identified.

Preferred exogenous activation systems include S-9 liver microsomal enzyme preparations, microsomal enzymes substantially purified from S-9 preparations, or combinations of recombinant liver microsomal enzymes. In a particularly preferred embodiment, the S-9 preparation is derived from a preparation of human or rat liver.

Unless otherwise noted, the terms used throughout this specification and the appendant claims generally have their usual meaning as understood by those of ordinary skill in the art (see, for example, *The Dictionary of Cell & Molecular Biology*, $3^{rd}$ Edition, by Lackie, J. M and Dow, J. A. T., published in 1999 by Academic Press (New York); and *Instant Notes in Molecular Biology*, by Turner, P. C. et al., published in 1998 by BIOS Scientific Publishers Limited). The following terms are intended to have the following general meanings as they are used herein:

bioluminescence is the phenomenon whereby light is produced by a living organism, resulting from a reaction catalyzed by, for example, bacterial luciferase or firefly luciferase;

a cassette is a pre-existing structure into which an insert can be moved, and is generally used to refer to certain vectors, e.g., that contain all that is needed for expression of the contiguous DNA sequence (expression cassette);

a codon is a coding unit (triplet of bases) of DNA that specifies the amino acid to be incorporated into the polypeptide during protein synthesis;

a frameshift mutation is an insertion or deletion in an open reading frame in a DNA sequence;

a gram-negative bacterium is a bacterium with a thin peptidoglycan cell wall bounded by an outer membrane containing endotoxin (lipopolysaccharide), such as, *Salmonella typhimurium*;

a gram-positive bacterium is a bacterium with a thick cell wall containing teichoic and lipoteichoic acid complexed to the peptidoglycan;

an open reading frame (ORF) is a possible way of reading a DNA sequence which is capable of being translated into protein;

an operon is a group of bacterial genes with a common promoter that are controlled as a unit and produce a polycistronic mRNA (one piece), and consisting of at least two structural genes and control elements that regulate the transcription of those structural genes;

a plasmid (episome) is a small, independently replicating circular piece of cytoplasmic DNA found in prokaryotes and eukaryotes capable of autonomous replication that can be transferred from one organism to another, commonly used as cloning vectors (vectors of genes);

a point mutation is a mutation that causes the replacement of a single base pair with another base pair;

a promoter (constitutive) is a region of DNA to which RNA polymerase binds before initiating the transcription of DNA into RNA;

a restriction enzyme (endonuclease) is one of a class of bacterial enzymes that can cut DNA at specific sites;

a restriction site is a site in DNA that can be cut by a restriction enzyme;

a transition is a point mutation in which either a purine is mutated to another purine, or a pyrimidine is changed to another pyrimidine;

a transposon (transposable element) is a small, mobile DNA sequence that can replicate and insert copies at random sites within chromosomes;

a transversion is a point mutation in which a purine is substituted by a pyrimidine or vice versa;

a vector is a plasmid that can be used to transfer a DNA sequence(s) from one organism to another.

Unless otherwise noted, throughout this description and the appendant claims: % is percent; 2A is 2-anthramine; AGE is agarose gel electrophoresis; ATCC is American Type Culture Collection; ° C. is degrees Centigrade; $cm^2$ is centimeter(s) squared; DMSO is dimethylsulfoxide; DNA is deoxyribonucleic acid; EDTA is ethyldiaminetetraacetic acid; $FMNH_2$ is reduced flavin mononucleotide; kb is kilobase(s); KCN is potassium cyanide; KV is kilovolt(s); mg is milligram(s); mL is milliliter(s); mM is millimolar (concentration); MNNG is N-methyl-N'-nitro-nitrosoguanidine; mRNA is messenger ribonucleic acid; V is volt(s); NaN is sodium azide; ng is nanogram(s); nm is nanometer(s); OD is optical density, such as $OD_{600}$ which is the optical density at 600 nm; PBS is Dulbecco's phosphate buffered saline; rlu means relative luminescence unit; rpm is revolutions per minute; sec is second(s); SOC (Super Optimal Catabolite) medium is 2% bactotryptone, 0.5% yeast extract, 10 mM NaCl, 2.5 mM KCl, 20 mM glucose, 10 mM $MgCl_2$, and 10 mM $MgSO_4$; TAE buffer is 40 mM Tris-Acetate, 2 mM $Na_2EDTAx2H_2O$); μg is microgram(S); μL is microliter(S); μsec is microsecond(S); UV is ultraviolet; μW is microwatt(s); VBBH medium is 4 mg/mL glucose, 20 μL/mL VB concentrate (50x), 7.5 μg/mL biotin, and 5 μg/mL histidine; and Vogel-Bonner salt concentrate is 1% $MgSO_4 \cdot 7H_2O$, 10% citric acid monohydrate, 50% $K_2HPO_4$, and 17.5% $NaNH_4HPO_4 \cdot 4H_2O \cdot ATCC$ is located at 10801 University Boulevard, Manassas, Va., 20110-2209, USA. Boehringer Mannheim (Boehringer) is located in Mannheim, Germany. DIFCO™ (w/BD Biosciences) is located in Sparks, Md., USA. Epicentre Technologies (Epicentre) is located in Madison, Wis., USA. Life Technologies is located in Rockville, Md., USA. Molecular Devices is located in Sunnyvale, Calif., USA. Molecular Toxicology is located in Boone, N.C. USA. New England Biolabs (NEB) is located in Beverly, Mass., USA. QIAGEN is located in Valencia, Calif., USA. Roche Molecular Biochemicals (Roche) is located in Indianapolis, Ind., USA. Sigma is located in St. Louis, Mo., USA. Sigma-Genosys is located in St Louis, Mo., USA. Stratagene is located in La Jolla, Calif., USA. Xenometrix is located in Boulder, Colo., USA.

BRIEF DESCRIPTION OF THE DRAWINGS

For a better understanding of the invention as well as other objects and further features thereof, reference is made to the following detailed description of various preferred embodiments thereof taken in conjunction with the accompanying drawings wherein:

FIG. 1 is a schematic representation of a preferred embodiment of the present invention. It depicts plasmids used for the development of bacterial tester strains for use in the assays of the present invention.

FIG. 2 is a schematic representation of a preferred embodiment of the present invention. It depicts levels of bioluminescence during growth phases of bacterial culture where bioluminescence is plotted against both time and cell density.

FIG. 3 is a schematic representation of a preferred embodiment of the present invention. It depicts the influence of KCN on bioluminescence.

FIG. 4 is a schematic representation of a preferred embodiment of the present invention. It depicts the detection of bioluminescent revertants after treatment with an amount of the known mutagen MNNG.

FIG. 5 is a schematic representation of a preferred embodiment of the present invention. It depicts the detection of bioluminescent revertants based on the independent exposure of bacterial cells of the invention to amounts of two known agents, namely, MNNG and NaN. It also depicts, in the rightmost frame, the bioluminescence of the revertants exposed to 2A with, and without, the substantially simultaneous exposure to an amount of S-9.

FIG. 6 is a schematic representation of a preferred embodiment of the present invention. It depicts plasmids used for the development of bacterial tester strains for a bioluminescent β-lactamase assays of the present invention.

FIG. 7 is a schematic representation of a preferred embodiment of the present invention. It depicts the influence of mucAB expression on UV sensitivity of *Salmonella typhimurium*.

FIG. 8 is a schematic representation of a preferred embodiment of the present invention. It depicts the detection of mutagenic activity of MNNG using the bioluminescent β-lactamase assay of the present invention.

DETAILED DESCRIPTION OF THE INVENTION

The Ames Assay employs a set of histidine mutants of *Salmonella typimurium*. These mutants each have a unique reversible point mutation in one of the histidine genes which renders them incapable of producing histidine. The mutants are exposed to a test agent (putative mutagen) in the presence of a mammalian (generally, rat or human) liver homogenate (S-9 fraction, liver microsomal enzymes) to enable activation of the test agent, and the number of revertant colonies (able to produce histidine) induced by the test agent in the set of histidine-requiring mutants is determined (Ames discloses that the results of testing a compound can be scored in two days). Control values are determined for: (a) the number of revertant colonies on plates with test agent but no S-9 mix, and (b) the number of colonies on plates with S-9 mix but no test agent. The values for the test and controls are then compared.

In the standard AMES Test (*Current Protocols in Toxicology*, Chapter 3. Genetic Toxicology: Mutagenesis and Adduct Formation, Chapter 3 Introduction, Unit 3.1 The *Salmonella* (Ames) Test for Mutagenicity) a set of six histidine (his⁻) mutant strains was developed (TA7001 (hisG1775), TA7002 (hisC9138), TA7003 (hisG9074), TA7004 (hisG9133), TA7005 (hisG9130), and TA7006

(hisC9070)) to determine the mutational spectrum of a particular mutagen, i.e., the reversion of such strains by unique base-pair substitutions (see, for example, Gee, P. et al., 1994). Each of the six strains detects one of the following mutations: T:A→C:G, T:A→A:T, T:A→G:C, C:G→T:A, C:G→A:T, or C:G→G:C and, as such, each shows a low spontaneous reversion frequency (see, for example, *Current Protocols in Toxicology,* Chapter 3. Genetic Toxicology: Mutagenesis and Adduct Formation, Chapter 3 Introduction, Unit 3.1 The *Salmonella* (Ames) Test for Mutagenicity, Support Protocol 4: Genetic Analysis of Strains). The treatment of these cells with mutagens results in an increased number of revertants (his$^+$) capable of producing endogenous histidine unlike the non-reverted cells (his$^-$). The revertants are detected as colonies of growing cells on a background lawn of his$^-$ cells.

The bioluminescent modification of the AMES Assay provided by the present invention utilizes genetically modified AMES Salmonella tester strains expressing the lux (CDABE) operon preferably from *Xenorhabdus luminescens* (see, for example, Johnston, T. C. et al., 1990; Szittner, R. & Meighen, 1990; and Xi, L. et al., 1991).

The luxCDABE operon from *Xenorhabdus luminescens* (ATCC Number 29999, originally contributed by G. M. Thomas) includes genes coding for luciferase (A and B) and a fatty acid reductase (C, D and E) (Frackman, S. et al., 1990). The fatty acid reductase generates an endogenous substrate which is cleaved by the luciferase. This reaction requires energy supplied in the form of endogenous FMNH$_2$ and produces visible and measurable bioluminescence (Stewart, G. S. and Williams, P., 1992). An advantage of the assays of the present invention system is the stability at 37° C., which allows for performing experiments at the physiological temperature of 37° C. In addition, the presence of fatty acid reductase provides a closed system without the need to supplement the bioluminescent reaction with exogenous substrate. Those skilled in the art will readily realize, based upon the present description, that any other suitable luciferases isolated from any suitable microorganisms can also be used in the assays of the present invention, e.g., present assays are not limited to the use of the lux(CDABE) from *Xenorhabdus luminescens* (Stewart, G. S. and Williams, P., 1992).

As those skilled in the art will appreciate from the present description, any suitable methods can be used to prepare the lux(CDABE) expression cassette of the present invention. In a preferred embodiment of the present invention, kanamycin transposon EZ::TN<KAN-2> (Epicentre) is used as a base for the lux(CDABE) expression cassette, where the expression of the kanamycin resistance gene (kanamycin phosphotransferase) is regulated by a constitutive promoter, and the expression of the lux(CDABE) is driven by read-through from the kanamycin phosphotransferase promoter. The read-through expression of lux(CDABE) has been described (see, for example, Winson, M. K., et al., 1998). Any suitable of a variety of constitutive promoters can be used to control expression of the lux(CDABE). An advantage of the preferred cassette of the present invention is its relative small size and ability to be excised with PvuII restriction endonuclease as a blunt ended fragment of DNA. This allows relatively simple insertion of the lux(CDABE) expression cassette into any suitable of a variety of plasmids. In addition, the presence of the kanamycin resistance gene is useful for the selection of transformed cells in strains with the ampicillin resistance phenotype.

The luminescent tester strains have been generated using the lux(CDABE) expression cassette on plasmids. Alternatively, the lux(CDABE) expression cassette can be inserted into the bacterial chromosome. For example, the transposon containing the lux(CDABE) expression cassette can be used with an enzyme transposase (Epicentre) to form transposome, and inserted into the chromosome. Alternatively, any other suitable means for generating transposons can be used in the present invention (see, de Lorenzo, V., et al., 1993, and 1990). As those skilled in the art will appreciate based on the present description, the delivery of the lux(CDABE) operon can also be achieved using phage vectors as described in *Current Protocols in Molecular Biology,* John Wiley & Sons, Inc. (2000), Chapter 1. *Escherichia coli,* Plasmids, and Bacteriophages).

Those skilled in the art will understand, based upon the present description, that the introduction of the lux(CDABE) into bacterial cells for use in the present assays can be achieved using various suitable techniques and that, the important condition for the successful construction of the bacterial tester strain is to achieve a stable bioluminescence only in cells that are metabolically active (*Current Protocols in Molecular Biology,* Chapter 1. UNIT 1.8 Introduction of Plasmid DNA into Cells).

Any suitable cells can be used for the development of the high throughput mutagenicity assays of the invention. Original Ames' strains of *Salmonella typhimurium* (Ames, B. N., 1973) were used for the development of a preferred embodiment of the bioluminescent bacterial reversion mutation assays provided by the present invention. Such strains were selected, e.g., because they provide data that substantially correlate with the original Ames Test (Vollmar, J. and Edler, L., 1990). Other strains such as *E. coli* WP2 (McCalla, D. R. et al., 1975) can also used in the assays of the present invention.

Those skilled in the art will appreciate, based upon the present description, that any bacterial tester strain suitable for bacterial reversion mutation assays can be used in the assays of the present invention. For example, in a preferred embodiment, a β-lactamase reversion system is employed. In addition, the endpoint of the assays of the present invention can be any event leading to the maintenance of active metabolism, i.e., is not limited to the reversal of a point mutation.

Moreover, any organism in which the systems provided by the invention can be used to ultimately emit light such as, for example, yeast (*Saccharomyces cerevisiae*) can be utilized in the assays of the present invention. For example, luxa and luxB can be fused to form a functional luciferase in yeast (Van der Sand, S. T. et al., 1992). As those skilled in the art will appreciate in light of the present description, there are a number of known assays that can be modified in accordance with the present invention to provide improved utility (e.g., the deletion recombination assay described by Schiestl, R. H., 1989). The assays of the present invention can also use mammalian cells and, those skilled in the art will understand from the present description how to make and use such cells.

Those skilled in the art will appreciate from the present description that any suitable assay format can be used in the assays of the present invention. In a preferred embodiment, a multi-well plate is used, as it is advantageous for achieving high throughput using currently available tools. The assays of the present invention can be performed in either a non-liquid (e.g., a bottom agar with cells plated in top soft agar) or a liquid format (e.g., in a liquid medium). In a preferred embodiment, the assay uses a bottom agar with the test cells plated in top soft agar. Where using a liquid medium format, mixing, stirring, and/or circulation of the medium should be optimized to preclude undesirable cell sedimentation which could then lead to the phenomenon of quorum sensing (Surette, M. G. and Bassler, B. L., 1998) that would impair the growth of revertants and likely provide misleading data. In another embodiment, a viscosity-increasing agent, e.g., carboxymethylcellulose, is employed in the medium in place of agar. Further yet, in another preferred embodiment, a biofilm with a bacterial tester strain is used.

Any suitable metabolic activation system can be used in the assays of the present invention to activate the test agent, where so desired. Preferred metabolic activation systems include, for example, S-9. The preparation and conditions for use of this preparation are well known in the art (*Current Protocols in Toxicology*, Unit 3.1 The *Salmonella* (Ames) Test for Mutagenicity, Support Protocol 5: Preparation of Metabolic Activation System (S-9); Ames, B. N. et al., 1975; and Maron, D. M. and Ames, B. N., 1983). In addition, those skilled in the art will understand that any one, or combination, of the enzymes that a typical S-9 preparation contains, that play a role in activating a given test agent, may also be used in the assays of the present invention, as the case may be, as so desired.

Those skilled in the art will understand, based on the present description, how to select suitable reagents and conditions of the assays so as to achieve the desired results (see, for example, *Current Protocols in Toxicology*, Chapter 3. Genetic Toxicology: Mutagenesis and Adduct Formation, Chapter 3 Introduction, Unit 3.1 The *Salmonella* (Ames) Test for Mutagenicity, Reagents and Solutions (Contributed by Errol Zeiger, Environmental Toxicology Program/National Institute of Environmental Health Sciences Research Triangle Park, N.C., and Kristien Mortelmans, SRI International, Menlo Park, Calif.), and TABLES (Table 3.1.1 Commonly Used *Salmonella* Tester Strains and Their Genotypes, Table 3.1.2 Recommended Positive Control Chemicals and Test (for various known tester strains), Table 3.1.3 Spontaneous Control Values for the *Salmonella* Tester Strains, and Table 3.1.4 Troubleshooting Guide for Ames Test).

Any suitable means for detecting biolumiescent cells can be used in the assays of the present invention. For example, in a preferred embodiment, a photon counting charge-coupled device (CCD) camera (Lumi-Imager, Boehringer) is used to count bioluminescent microcolonies (Silcock, D. J. et al., 1992). Alternatively, gross colonization patterns can be recorded by long exposures of conventional 35 mm film or X-ray film.

In one aspect of the present invention, the treatment of the bacterial cells (TA1535 (hisG46), TA100 (hisG46), or TA98 (hisD3052), see Ames, B. N. et al., 1975) of the invention (comprising a heterologous lux(CDABE) gene complex under the control of a constitutive promoter) with mutagens results in an increased number of HIS$^+$ cells (revertants). Since his genes are essential for the biosynthesis of histidine, the revertant his$^+$ cells are capable of producing endogenous histidine and are detected as colonies of growing cells on a background lawn of his$^-$ cells. In this embodiment of the bioluminescent assays of this invention, the lack of histidine in the medium leads to a cessation of metabolic activities in his$^-$ cells resulting in an inability to generate sufficient levels of FMNH$_2$ to produce bioluminescence. In contrast, his$^+$ revertant cells are capable of maintaining metabolic activities and producing bioluminescence even in the absence of histidine.

In another aspect of the present invention, the treatment of the *Escherichia coli* strain WP2 cells (carrying a point mutation in the tryptophan gene, see Green, M. H. L. & Muriel, W. J., 1976; Wilcox, P. et al., 1990; and Dunkel, V. C. et al., Environ. Mutagen. 6 (Suppl. 2): 1–25 (1984)) of the invention (comprising a heterologous lux(CDABE) gene complex under the control of a constitutive promoter) (WPpBRTNlux1) with mutagens results in an increased number of trp$^+$ cells (revertants). Since the trp gene is essential for the biosynthesis of tryptophan, the revertant trp$^+$ cells are capable of producing endogenous tryptophan and are detected as colonies of growing cells on a background lawn of trp$^-$ cells. In this embodiment of the bioluminescent assays of this invention, the lack of tryptophan in the medium leads to a cessation of metabolic activities in trp$^-$ cells resulting in an inability to generate sufficient levels of FMNH$_2$ to produce bioluminescence. In contrast, trp$^+$ revertant cells are capable of maintaining metabolic activities and producing bioluminescence even in the absence of tryptophan.

In yet another aspect of the present invention, the treatment of the *Salmonella typhimurium* tester strains (e.g., TA1535) of the invention (comprising a heterologous lux (CDABE) gene complex under the control of a constitutive promoter)(e.g., pBRTNluxAM, or pBRTNluxAMmuc631, as the case may be, with both carrying a gene encoding kanamycin, and each carrying a point mutation in the β-lactamase gene (conferring an ampicillin sensitive phenotype)) with mutagens results in an increased number of ampicillin resistant cells (revertants). Since ampicillin resistance is critical for survival in ampicillin-containing medium, the revertant cells are metabolically active in such medium and are detected as colonies of growing cells on a background lawn of ampicillin-sensitive cells. In this embodiment of the bioluminescent assays of this invention, the lack of a proper functioning β-lactamase given the presence of ampicillin in the medium leads to a cessation of metabolic activities in these ampicillin-sensitive cells resulting in an inability to generate sufficient levels of FMNH$_2$ to produce bioluminescence. In contrast, the revertant cells are capable of maintaining metabolic activities and producing bioluminescence even in the presence of ampicillin.

Lyophilized samples of each of the following microorganisms disclosed herein were deposited on Dec. 7, 2000 by Pfizer, Inc., with the ATCC under the terms of the Budapest Treaty:

*Salmonella typhimurium* TA1535lux (comprising pBRTNlux1) (UC25447, SA1535pBRTNlux1) assigned deposit number PTA-2760;

*Salmonella typhimurium* TA100lux (comprising pBRTNlux2) (UC25448, SA100pBRTNlux2) assigned deposit number PTA-2761;

*Salmonella typhimurium* TA98lux (comprising pTNlux2) (UC25449, SA98pTNlux2) assigned deposit number PTA-2762;

*Salmonella typhimurium* TA2220lux (comprising pBRTNluxAM1) (UC25450, SAl 535pBRTNluxAM1) assigned deposit number PTA-2763;

*Salmonella typhimurium* TA2211lux (comprising pBRTNluxAMmuc631) (UC25451, SA1535pBRTNluxAMmuc631) assigned deposit number PTA-2764; and

*Escherichia coli* WP2lux (comprising pBRTNlux1) (UC25452, WPpBRTNlux1) assigned deposit number PTA-2765.

All restrictions on the availability to the public of the microorganism cultures so deposited will be irrevocably removed upon the issuance of a patent from the specification of the present invention.

These novel bacterial strains are used in the subject processes because, for example, they have a suitable frequency of spontaneous reversion to the appropriate wt gene, as the case may be), they have the improved property (in comparison to those microorganisms used in the original and modified Ames Tests) of being able to emit an amount of bioluminescence after exposure to a mutagen, e.g., carcinogen, greater than the amount, if any, produced by the microorganism in the absence of the mutagen, or in the presence of the mutagen but the absence of the exogenous metabolic activation system (e.g., S-9 mix prepared from rat or human liver microsomes), as the case may be, and the results (mutagenicity of a given test agent) of this bioluminescent modification of the Ames test substantially correlate with those where one uses the original Ames Test, or the spiral modification thereof.

Those skilled in the art will appreciate that, based upon the present description, the plasmids suitable for use in the present invention, including those listed in Table 1 provided hereinbelow, can be isolated from the deposited microorganisms using conventional techniques. Hence, where so desired, those skilled in the art can use a different microorganism as a tester strain and transform this microorganism with the desired plasmid isolated from the appropriate deposited microorganism. In addition, those skilled in the art will also understand, based on the present description, how to remove the lux(CDABE) gene complex from the desired deposited microorganism and ligate it into a suitable vector or plasmid of choice for any particular mutagenicity assay of the present invention.

Accordingly, the present invention provides plasmids carrying the bacterial lux operon and a selectable marker (to select the population of transformed bacterial cells) such as, for example, a gene which confers resistance to β-lactam antibiotics.

Any suitable method can be used to prepare the lux (CDABE) expression cassette. Those skilled in the art, based upon the present description, will understand how to use conventional techniques to prepare the expression cassette, and to ligate the cassette into a suitable plasmid for the ultimate transformation of a target bacterial cell. A preferred method is shown in the examples provided hereinbelow.

As those skilled in the art can understand from the present description, the processes of the present invention are readily carried out and can result in substantial cost-savings, when compared with the Ames Test, or with the described modifications of the Ames Test, in terms of the decreased quantity of test agent required, the decreased amount of manual labor necessary to count revertant colonies against a lawn of non-revertant colonies given the sensitivity of bioluminescence, the decreased amount of time necessary to reach a result, and the readily scalability to high throughput formats, while substantially correlating with data gathered through use of such Ames Tests, thus permitting reasonable comparisons with such data. Given that numerous data have been generated through the use of the Ames Test, those skilled in the art would desire that any suitable improvements thereto be directly comparable in terms of readout of genotoxicity.

The present invention provides novel assays for determining whether a particular agent is a mutagen (causes reversion (or forward mutation, as the case may be, as would be understood by one of skill in the art, based on the present description)), or genotoxic. These assays preferably employ the standard bacterial strains used in the Ames Test, e.g., strains of Salmonella typhimurium having point mutations in histidine genes; however, these bacterial cells have now been genetically modified to be able to produce bioluminescence, or emit light, under certain conditions. Use of these novel bacterial strains in an Ames Test format, enables the use of much less (ng/ug versus g) of the test agent (or putative mutagen), as well as a relatively immediate readout of the number of revertant colonies, without the laborious and cumbersome manual counting of these colonies. Unlike the modified Ames Tests described above, the present assays or tests do not require, for example, detection of revertants based on an estimate from bacterial growth curves or by a dilution plating scheme.

The detailed examples provided below show that the mutagenicity of a test agent, e.g., a proposed pharmaceutical product, can be ascertained through use of the assay of the invention. Table 1, provided immediately below, is a listing of the plasmids used in the preparation of the plasmids used to prepare the novel bacterial test strains for use in the assays of the invention.

TABLE 1

Plasmids.

| PLASMID | FEATURES | SOURCE |
| --- | --- | --- |
| pSB417 | contains lux (CDABE) | Dr. Simon Swift, University of Nottingham, Nottingham, UK |
| pUC19 | cloning vector | NEB |
| pBR322 | cloning vector | NNEB |
| pFN467 | cloning vector | ATCC |
| pBKCMV | cloning vector | Stratagene |
| pTNKan | kanamycin transposon in pUC19 | prepared as described herein |
| plux | lux (CDABE) in pBKCMV | prepared as described herein |
| pTNlux | lux (CDABE) in pTNKan, source of lux(CDABE) expression cassette | prepared as described herein |
| pBRTNlux cassette | lux (CDABE) expression in pBR322 | prepared as described herein |
| pFNTNlux cassette | lux (CDABE) expression in pFN467 | prepared as described herein |
| pUCmuc | mucAB expression cassette in pUC19 | prepared as described herein |
| pBRTNluxAM | bioluminescent β-lactamase mutagenicity assay system | prepared as described herein |
| pBRTNluxAMmuc631 | improved bioluminescent β-lactamase mutagenicity assaysystem | prepared as described herein |

In addition, Table 2, provided immediately below, is a listing of bioluminescent bacterial tester strains prepared as described in the present description, and for use in the assays of the present invention. The strains include those with point mutations in histidine genes and those with point mutations in a β-lactamase gene (in the codon for the active site serine).

TABLE 2

Bioluminescent bacterial tester strains.

| STRAIN DESIGNATION | GENETIC BACKGROUND | EMBODIMENT |
| --- | --- | --- |
| TApTNlux | TA1535 | Biolum AMES |
| TApBRTNlux | TA1535 | Biolum AMES |
| TApFNTNlux | TA1535 | Biolum AMES |

TABLE 2-continued

Bioluminescent bacterial tester strains.

| STRAIN DESIGNATION | GENETIC BACKGROUND | EMBODIMENT |
|---|---|---|
| SA100pTNlux | TA100 | Biolum AMES |
| SA100pBRTNlux | TA100 | Biolum AMES |
| SA100pFNTNlux | TA100 | Biolum AMES |
| SA98pTNlux | TA98 | Biolum AMES |
| SA98pBRTNlux | TA98 | Biolum AMES |
| SA98pFNTNlux | TA98 | Biolum AMES |
| WPpTNlux | WP2 | Biolum AMES |
| WPpBRTNlux | WP2 | Biolum AMES |
| WPpFNTNlux | WP2 | Biolum AMES |
| SApBRTNluxAM | TA1535 | Biolum β-lac |
| SApBR322TnluxAMmuc631 | TA1535 | Biolum β-lac |

The present invention is illustrated by the following examples. The foregoing and following description of the present invention and the various embodiments are not intended to be limiting of the invention but rather are illustrative thereof. Hence, it will be understood that the invention is not limited to the specific details of these examples.

EXAMPLE I

Embodiment of the Bioluminescent Mutagencity Assay 1.1. Construction of a lux(CDABE) Expression Cassette To achieve a stable luminescence output in dark (non-luminescent) gram negative bacteria such as *Salmonella typhimurium* (*Salmonella choleraesuis* subsp. Choleraesuis (Smith) Weldin serotype *Typhimurium* deposited as *Salmonella typhimurium*, ATCC Number 29629 (TA1535), contributed by P. A. Pattee)) the lux(CDABE) operon from *Xenorhabdus luminescens* (*Photorhabdus luminescens* subsp. *Luminescens* (Thomas and Poinar 1979) Boemare et al. deposited as *Xenorhabdus luminescens*, ATCC Number 29999, contributed by G. M. Thomas) was placed under the control of a strong promoter residing on kanamycin transposon EZ::TN<KAN-2> (Epicentre). The transposon was purchased as a linear PvuII site flanked DNA fragment. The vector pUC19 (NEB) was digested with PvuII (NEB). Twenty μl of the reaction mix consisting of 5 μg DNA and 100 units PvuII in presence of manufacturer supplied buffer was incubated at 37° C. for 1 hour. The PvuII digestion produced two fragments (2.2 kb and 0.6 kb) that were separated using agarose gel electrophoresis (*Current Protocols in Molecular Biology*, Unit 2A Agarose Gel Electrophoresis). Briefly, the sample was loaded onto a 0.8% agarose gel and run in TAE buffer at 50 V for 1 hour. Bands were stained using ethidium bromide (5 ng/mL for 30 min) and visualized on transluminator at 2500 μW/cm$^2$. An agar plug containing the 2.2 kb fragment was excised. The DNA was purified from the agar gel using QIAquick kit (QIAGEN). To remove 5' phosphate groups, the isolated DNA was solubilized in 18 μl buffer 2 (NEB) and incubated with 2 μl calf intestinal alkaline phosphatase (NEB) at 37° C. for 2 hours. The DNA was purified using QIAquick kit (QIAGEN) and resuspended in 10 μl of sterile water. The isolated 2.2 kb PvuII flanked fragment of pUC19 contained the origin of replication and β-lactamase as selection marker. The kanamycin transposon EZ::TN<KAN-2> was ligated into the PvuII flanked fragment of pUC19. The ligation reaction was performed using Rapid DNA ligation Kit (Roche). The transformation of *Escherichia coli* cells (UltraMAx™ DH5α-FT™ Competent cells, Life Technologies) with ligation mix was performed according a protocol recommended by the manufacturer. It produced colonies of cells carrying pTNKan that were resistant against ampicillin and kanamycin.

To allow a read through control of the lux(CDABE) operon from kanamycin resistance gene promoter, the lux(CDABE) sequence was placed downstream of the kanamycin resistance gene. Because of absence of appropriate cloning sites, the lux(CDABE) isolated from pSB417 as EcoRI fragment was first ligated into the EcoRI site in a cloning vector pBKCMV (Stratagene). Briefly, reaction mixes (total volume of 20 μl) containing 5 μg Psb417 or pBKCMV and 100 units EcoRI (NEB) were incubated at 37° C. for 2 hours in presence of manufacturer supplied buffer. The digested samples were analyzed using AGE (*Current Protocols in Molecular Biology*, Unit 2A Agarose gel electrophoresis). The EcoRI digestion of pSB417 produced two fragments with approximate sizes 2.8 kb for vector and 5.7 kb for the promoterless lux(CDABE). In case of pBKCMV the EcoRI produced a single fragment approximately 4.5 kb. DNA fragments were separated using AGE. Samples were loaded onto a 0.8% agarose gel and run in TAE buffer at 50 V for 1 hour. Bands were visualized using transluminator at 2500 Uw/cm$^2$ and agar plugs containing the 5.7 kb fragment of pSB417 and the linear 4.5 kb Pbkcmv were excised. The DNA was purified from the agar using QIAquick kit (QIAGEN). To remove 5' phosphate groups from the promoterless lux(CDABE) cassette, the isolated DNA was solubilized in 18 μl buffer 2 (NEB) and incubated with 2 μl calf intestinal alkaline phosphatase (NEB) at 37° C. for 2 hours. The dephosphorylated lux(CDABE) cassette was purified using QIAquick kit (QIAGEN) and resuspended in 10 μl of sterile water. The subsequent ligation reaction brought together pBKCMV and lux(CDABE) cassette and produced plasmid named plux. The ligation reaction was performed using Rapid DNA ligation Kit (Roche). The transformation of *E. coli* cells (UltraMAx™ DH5α-F™ Competent cells, Life Technologies) with ligation mix was performed according a protocol recommended by the manufacturer. It produced bioluminescent colonies of cells carrying plux that were resistant against kanamycin.

The orientation of lux(CDABE) relative to the lac promoter on Pbkcmv was determined using restriction mapping (*Current Protocols in Molecular Biology*, Chapter 3. Enzymatic Manipulation Of DNA and RNA, Section II Restriction Mapping). The plasmids isolated from 10 randomly picked colonies were digested with ClaI (NEB). The reaction conditions were 2 μg DNA, 100u restriction enzyme and appropriate buffer in total volume 20 μl. Samples were resolved using AGE (0.8% agarose gel, TAE buffer, 50V). The plasmid containing lux(CDABE) cassette flanked with 5' BamHI and 3' PstI was selected for insertion into pTNKan.

The lux(CDABE) was excised with BamHI and PstI in reaction mix consisting of 5 μg DNA, 100 units BamHI, 100 units PstI and buffer 2 (NEB). The digestion reaction gave 2 bands 5.4 kb containing vector pBKCMV and 5.7 kb promoterless lux(CDABE) cassette. The pTNkan was linearized with BamHI and PstI in reaction mix consisting of 5 μg DNA, 100 units BamHI, 100u PstI and buffer 2. The samples were resolved using AGE (Current Protocols in Molecular Biology, Unit 2A Agarose gel electrophoresis). The lux(CDABE) fragment and linearized pTNKan were isolated form the gel using QIAquick kit (QIAGEN). Subsequently, the BamHI-PstI flanked lux(CDABE) fragment was ligated into BamHI and PstI cut pTNkan. The ligation reaction was performed using Rapid DNA ligation Kit (Roche). The transformation of *Escherichia coli* cells (UltraMAx™ DH5α-FT™ Competent cells, Life Technologies) with ligation mix was performed according a protocol recommended by the manufacturer. It produced bioluminescent colonies of cells carrying pTNlux that were resistant against ampicillin and kanamycin cytotoxicity. The final plasmid was named pTNlux (FIG. 1). The lux (CDABE) expression cassette consisting of kanamycin phosphotransferase and lux(CDABE) can be easily excised from pTNlux as Pvull fragment.

1.2. Construction of Low and Medium Copy Plasmids Carrying lux(CDABE) Expression Cassette.

The pTNlux plasmid is based on pUC9 vector and it replicates in the cytoplasm in high copy numbers (1000–3000 copies/cell). To determine the influence of plasmid copy number on bioluminescent output, additional plasmids were constructed with various origins of replication.

The medium copy number plasmid (100–300 copies/cell) was constructed based on the vector pBR322 (NEB). The lux(CDABE) expression cassette was excised from pTNlux with Pvull (NEB) in reaction mix consisting of 5 µg DNA, 100 units Pvull, and buffer 2 (NEB). The reaction was incubated at 37° C. for 1 hour. The vector pBR322 was linearized with EcoRV (NEB). The reaction consisted of 5 µg DNA, 100 units EcoRV, and buffer 2 supplied by manufacturer. The reaction was incubated at 37° C. for 1 hour. Products of digestion reactions were resolved using agarose gel electrophoresis (*Current Protocols in Molecular Biology*, Unit 2A Agarose gel electrophoresis). The lux (CDABE) expression cassette and linearized pBR322 DNA bands were isolated from the agar gel using QIAquick kit (QIAGEN). To prevent recircularization of the vector, 5' phosphate groups were removed by incubating the linearized vector DNA with 2 µl calf intestinal alkaline phosphatase in presence of buffer 2 (NEB) in total reaction volume of 20 µl at 37° C. for 2 hours. The dephosphorylated lux(CDABE) expression cassette was purified using QIAquick kit (QIAGEN) and resuspended in 10 µl of sterile water. Subsequently, the lux(CDABE) expression cassette was ligated into pBR322. The ligation reaction was performed using Rapid DNA ligation Kit (Roche). The transformation of *E. coli* cells (UltraMax™ DH5α-FT™ Competent cells, Life Technologies) with ligation mix was performed according a protocol recommended by the manufacturer. It produced bioluminescent colonies that were resistant against ampicillin and kanamycin cytotoxicity. The final plasmid was named pBRTNlux (FIG. 1).

The low copy plasmid (2-6 copies/cell) was constructed based on the vector pFN467 (ATCC Number 86962, contributed by P. Sankar). The lux(CDABE) expression cassette was excised from pTNlux with Pvull (NEB) in reaction mix consisting of 5 µg DNA, 100 units Pvull, and buffer 2 (NEB). The reaction was incubated at 37° C. for 1 hour. The vector pFN467 was linearized with Smal (NEB). The reaction consisted of 5 µg DNA, 100 units Smal, and buffer 2 supplied by the manufacturer. The reaction was incubated at 37° C. for 1 hour. Both digestion reactions were resolved using agarose gel electrophoresis (Current Protocols in Molecular Biology, Unit 2A Agarose gel electrophoresis). The lux(CDABE) expression cassette and linearized Pfn467 DNA bands were isolated from the agar gel using QIAquick kit (QIAGEN). To prevent recircularization of the vector, 5' phosphate groups were removed by incubating the linearized Pfn467 DNA with 2 µl calf intestinal alkaline phosphatase in presence of buffer 2 (NEB) in total reaction volume of 20 µl at 37° C. for 2 hours. The dephosphorylated molecules of pFN467 were purified using QIAquick kit (QIAGEN) and resuspended in 10 µl of sterile water. Subsequently, the lux(CDABE) expression cassette was ligated into pFN467. The ligation reaction was performed using Rapid DNA ligation Kit (Roche). The transformation of *Escherichia coli* cells (UltraMax™ DH5α-FT™ Competent cells, Life Technologies) with ligation mix was performed according a protocol recommended by the manufacturer. The transformation produced bioluminescent colonies of cells that were resistant against ampicillin and kanamycin cytotoxicity. The final plasmid was named pFNTNlux.

1.3. Construction of Bioluminescent Bacterial Tester Strains.

*Salmonella* strains TA98, TA100 and TA1535, and *Escherichia coli* strain WP2 (Molecular Toxicology) were used for preparation of electrocompetent cells. One liter of NB medium was inoculated with 100 µl of frozen stock (OD=0.5, LB medium (Life Technologies) supplemented with 10% DMSO). The culture was grown at 37° C. until reaching the cell density $OD_{600}$=0.5–0.8. Salts were removed by series of washes. Cells were pelleted (4000 rpm at 4° C.) and resuspended in 1000 mL of ice cold sterile water. The resulting cell suspension was again pelleted and resuspended in 500 mL of ice cold water. After additional centrifugation cells were resuspended in 10 mL of ice cold 10% glycerol in water. The cell suspension in 10% glycerol was again pelleted and resuspended in 1 mL of ice cold 10% glycerol. Forty microliters aliquots of electrocompetent cells were flash frozen in liquid nitrogen and stored at −80° C.

The transformation of *Salmonella typhimurium* and *Escherichia coli* strains was performed using a BTX electroporator. Frozen aliquots of electrocompetent cells were slowly thawed on ice. Eighty microliters of the cell suspension and 5 µl of DNA solution (10 µg) were placed into an electroporation cuvette (0.2 cm electrode gap). The electroporation conditions consisted of three 99 µsec pulses with field strength 2.5 KV/cm. The electroporation mix was resuspended in 1 mL SOC medium (Life Technologies) and incubated at 37° C. for 1hour. The cell suspension was plated on agar plates supplemented with kanamycin or ampicillin to select for transformed cells. At least four independent luminescent colonies from each strain were further characterized and their capability of detecting mutagens was evaluated. Those strains were used for the development of the high throughput bacterial mutagenicity assay (Table 2).

1.4. Characterization of Bioluminescent Phenotype
1.4.1. Bioluminescent Output During Growth Phases of Bacterial Culture

*Salmonella* or *Escherichia coli* strains transformed with plasmids carrying the lux(CDABE) expression cassette were grown at 37° C. in 20 mL LB medium for up to 25 hr. Cultures were initiated with cells grown overnight on LB plates (Life Technologies). The cell density of liquid cultures was adjusted to $OD_{600}$=0.1 and initial levels of bioluminescence were recorded. Samples of 100 µl culture were collected in 1 hr intervals up to 11 hr. Additional samples were taken 25 hr after the culture initiation. The optical density and bioluminescence was measured at each time point using spectrophotometer (Spectramax, Molecular Devices) and photon counting CCD camera (Lumi-Imager, Boehringer). The bioluminescence increased with the cell density reaching maximum level at the entry into the stationary phase followed by a sharp decline (FIG. 2). In general, bacterial cells in the stationary phase limit their metabolic activity, and eventually die or form spores. The bioluminescent reaction requires energy in the form of endogenous reduced flavin mononucleotide $FMNH_2$ (Stewart, G. S. and Williams, P., 1992). Therefore, the drop of luminescence in the stationary phase can be explained as a consequence of cessation of metabolic activities. All strains carrying plasmid pTNlux, pBRTNlux, or pFNTNlux gave similar results. In contrast, Salmonella cells transformed with the original plasmid Psb417 showed growth dependent decrease of bioluminescent output suggesting growth dependent regulation of lux(CDABE) expression. These results provide an evidence that the lux(CDABE) expression cassette that utilize kanamycin transposon driven expression of lux(CDABE) is suitable to monitor metabolic activities of bacterial cells.

1.4.2. Bioluminescence is Dependent on Intracellular Sources of Energy

The lux(CDABE) driven bioluminescence is dependent on a steady supply of energy in the form of reduced flavin mononucleotide $FMNH_2$ (see, for example, Stewart, G. S. & Williams, P., 1992). Since the in vivo production of $FMNH_2$ in anaerobic organisms is coupled to the electron transport chain via an NADH and FMN reductase couple, the interruption of the respiratory chain should result in an instant loss of the bioluminescence. In general, cyanide interrupts the electron transport system by interaction with $Fe^{2+}$ of the cytochrome coxidase, the last link in the respiratory chain, resulting in the cessation of energy production. The potassium cyanide is widely used to study the dependence of biological processes on energy supply (see, for example, Skulachev, V. P., 1989).

To evaluate the role of energy supply on lux(CDABE) driven bioluminescence, we treated the Salmonella tester strain carrying plasmid pTNlux with potassium cyanide (FIG. 3). In our experiment, Salmonella strain TA1535 transformed with pBRTNlux was grown in liquid LB medium up to the cell density $OD_{600}$=0.6. Aliquots of 100 $\mu l$ culture were treated with a wide range of concentrations of potassium cyanide (Sigma) and the luminescence was immediately measured using photon counting CCD camera (Lumi-Imager, Boehringer). The bioluminescence decreased in a dose dependent fashion. This experiment clearly demonstrates the dependency of lux(CDABE) bioluminescence on energy supply in Salmonella typhimurium.

1.4.3. Detection of Mutagens Using an Embodiment of the Bioluminescent "Ames" Assays of the Invention.

In the standard Ames assay, the treatment of cells (TA1535, TA100, TA98) carrying a point mutation in one of the HIS genes (his⁻ cells) with mutagens results in an increased number of $HIS^+$ cells (revertants). Since HIS genes are essential for the biosynthesis of histidine, the revertant $HIS^+$ cells are capable of producing endogenous histidine and are detected as colonies of growing cells on a background lawn of his⁻ cells. In the bioluminescent assay, the lack of histidine in the medium leads to a cessation of metabolic activities in his⁻ cells resulting in an inability to generate sufficient levels of $FMNH_2$ to produce bioluminescence. In contrast, $HIS^+$ revertant cells are capable of maintaining metabolic activities and producing bioluminescence even in the absence of histidine. The bioluminescent modification of the AMES assay was performed in multi-well culture plates. In the assay, his⁻ cells were treated with tested compounds in a soft agar overlay containing a trace amount of histidine sufficient for cells to undergo 2–3 divisions (Current Protocols in Toxicology, Unit 3.1 The Salmonella (Ames) Test for Mutagenicity, Basic Protocol: Standard Plate Incorporation Test). Microcolonies of bioluminescent $HIS^+$ cells was visualized using photon counting CCD camera (Lumi-Imager, Boehringer) after a 30–40 hr incubation A frozen aliquot of cells was inoculated into 35 mL of LB medium supplemented with 50 $\mu g/mL$ kanamycin. The culture was grown at 30° C. for 15–18 hr (over night) under agitation (250 rpm). The overnight culture was diluted 3:1 with fresh kanamycin supplemented LB medium and grown at 37° C. until the cell density reached $OD_{600}$=0.5–0.6 (approximately 1–2 hr). Then, cells were washed twice in PBS (Dulbecco's Phospate buffered Saline, Life Technologies). The final cell density was adjusted to $OD_{600}$= 0.5 and the cells suspension was kept on ice. Aliquots of a sterile top agar solution (7.25 mL) were prepared using following components: VB concentrate (50×) 0.2 mL; biotin (170 $\mu g/mL$) 0.44 mL; histidine (6.7 mg/mL) 0.1 mL; kanamycin (40 $\mu g/mL$) 0.01 mL; glucose (2.6%) 2,59 mL; cells ($OD_{600}$=0.5) 2.5 mL). The top agar was prepared before the use and kept at 50° C. Since the exposure of Salmonella cells to a high temperature might decrease their viability, the unused top agar was discarded after 10 min. The assay was performed in minimal-agar 24- or 48-well plates prepared ahead of time. Each well contained 1 or 0.25 mL of minimal-agar, respectively. The minimal agar was prepared using 15 g Bactoagar (DIFCO), 4 g glucose, and 20 mL of 50× Vogel-Bonner salt concentrate in total volume of 1000 mL of distilled water. The sterilized agar was allowed to cool up to 50° C. in the water bath prior dispensing appropriate volumes into each well. The assay procedure was initiated by pipeting 17.5 $\mu l$ of PBS or in case of metabolic activation 17.5 $\mu l$ of S9 suspension onto the surface of minimal agar. Then, 10 $\mu l$ of the compound solution was added and the top agar containing cells was laid over the mix. To allow for a proper distribution of all components, the plate was agitated with vortexer at 900 rpm. Plates were incubated at 37° C. for 48 hrs. Luminescent microcolonies of revertants were visualized using photon counting CCD camera (Lumi-Imager, Boehringer). The increase in numbers of luminescent microcolonies in treated wells versus untreated wells indicated mutagenicity of tested compound (Table 3).

EXAMPLE III

High Throughput Embodiment of the Bioluminescent Mutagenicity Assay

To achieve high throughput with minimum compound requirement (less than 30 $\mu g$ per assay), a pre-incubation modification of the bioluminescent "Ames" assay of the present invention was developed. A frozen aliquot of cells was inoculated into 35 mL of LB medium supplemented with 50 $\mu g/mL$ kanamycin. The culture was grown at 30° C. for 15–18 hr (over night) under agitation (250 rpm). The overnight culture was diluted 3:1 with fresh kanamycin supplemented LB medium and grown at 37° C. until the cell density reached $OD_{600}$=0.5–0.6 (approximately 1–2 hr). Then, cells were washed twice in PBS (Dulbecco's Phosphate buffered Saline, Life Technologies). The cells were finally resuspended in VBBH medium (Glucose, 4 mg/mL; VB concentrate (50×), 20 $\mu l/mL$; biotin 7.5 $\mu g/mL$; histidine 5 $\mu g/mL$). The final cell density was adjusted to $OD_{600}$=0.65 and the cells suspension was kept on ice. Aliquots of a sterile top agar solution (7.25 mL) were prepared using following components: VB concentrate (50×) 0.2 mL; biotin (170 $\mu g/mL$) 0.44 mL; kanamycin (40 $\mu g/mL$) 0.01 mL; glucose (2.6%) 1,59 mL; PBS 2.5 mL; agar (2.4%), 2.59 mL). The top agar was prepared before the use and kept at 50° C. The assay was performed in minimal-agar 48-well plates prepared ahead of time. Each well contained 0.25 mL of minimal-agar. The minimal agar was prepared using 15 g Bactoagar (DIFCO), 4 g glucose, and 20 mL of 50× Vogel- Bonner salt concentrate in total volume of 1000 mL of distilled water. The sterilized agar was allowed to cool up to 50° C. in the water bath prior dispensing appropriate volumes into each well.

The exposure of cells with test article was done in 12.5 µl liquid medium per concentration tested for 4 hrs at 37° C. in 96-well V-bottom microtiter plates. The liquid medium contained 9 µl of cells suspension ($OD_{600}$=0.65), 2.2 µl PBS or S9, 1.25 µl tested article. After the incubation period 25 µl of the top agar was added into each well and immediately plated on 48-well plates containing minimum agar. To allow for a proper distribution of all components, the plate was agitated with vortexer at 900 rpm. Plates were incubated at 37° C. for 48 hrs. Luminescent microcolonies of revertants were visualized using photon counting CCD camera (Lumi-Imager, Boehringer). The increase in numbers of luminescent microcolonies in treated wells versus untreated wells indicated mutagenicity of tested compound (FIGS. 4 & 5).

EXAMPLE IV

Bioluminescent β-lactamase Embodiment

It has been shown that a point mutation in the β-lactamase could be used as genetic substrate in a reverse mutagenicity assay (see, for example, Lee, C -C, et al., 1994). In this system the mutation of A to G in the active site of β-lactamase (position 202) resulted in transformation of serine codon into glycine. This mutation resulted in ampicillin sensitive phenotype. Since the reverse mutation event G to A restored the wild type β-lactamase, the revertants were selected on agar plates supplemented with ampicillin. It has been shown that the β-lac assay is capable of detecting several model mutagens.

Construction of β-lactamase Bacterial Mutagenicity System

The bioluminescent version of the β-lac assay is based on pBRTNlux plasmid. This plasmid contains β-lactamase and lux(CDABE) expression cassette. The site directed mutagenesis was performed using QuickChange™ system (Stratagene). Two complimentary oligonucleotides (AtoGup: CGT TTT CCA ATG ATG GGC ACT TTT AAA GTT CTG; AtoGdown: CAG AAC TTT AAA AGT GCC CAT CAT TGG AAA ACG) containing the mutation A to G at the position 202 were custom synthesized (Sigma-Genosys). The template (10 ng of pBRTNlux), 125 ng of each primer, Dntp mix, and 2.5 units of PfuTurbo DNA polymerase were used to synthesize circular nicked DNA product containing the mutation. The synthesis was performed in 12 temperature cycles after a short denaturation step at 95° C. for 30 seconds. Each cycle consisted of 95° for 30 second, 55° C. for 1 minute and 68° C. for 15 minutes. The template DNA was removed by digestion with Dpnl restriction enzyme 37° C. for 17 hr. The purified nicked product was transformed into XL-1-Blue supercompetent cells (Stratagene) and plated on agar plates supplemented with 50 µg/mL kanamycin. Bioluminescent kanamycin resistant colonies were picked and their sensitivity to ampicillin was evaluated by plating on ampicillin supplemented LB plates (100 µg/mL). The plasmid conferring kanamycin resistance and ampicillin sensitivity was named pBRTNluxAM (FIG. 6). This plasmid was transformed into Salmonella strain TA 1535 giving the final strain SApBRTNluxAM. The ability of this strain to detect mutagens was confirmed using model compound MNNG.

EXAMPLE V

Preferred Embodiment of the β-lactamase Bacterial Mutagenicity System

Construction of an Improved β-lactamase System

The introduction of mucAB operon on the plasmid pKM101 into original AMES Salmonella strains TA1535 and TA1538 greatly increased the sensitivity of the assay (see, for example, McCann, J. et al., 1975). New strains TA100 and TA98, respectively, have become the most important strains used for mutagenicity testing. However, the bioluminescent P-lac tester strain SApBRTNluxAM is based on the original strain TA 1535 that is lacking the mucAB operon. Therefore, we constructed an improved β-lac system that contains mucAB operon. Since the presence of β-lactamase on plasmid pKM101 prohibited using original strains TA100 and TA98, we decided to isolate the mucAB expression cassette from pKM101 and insert it into the pBRTNluxAM. The mucAB was isolated from pKM101 plasmid present in TA 100 Salmonella strain using PCR. Two primers (MUC26low GCT TCA GGC GGC GGG CTT ACA M and MUC26up TCC CCGG GAC GCG GCC GGT TAC AGG GGA CAC T) were used to amplify a 2.6 kb fragment containing mucAB sequence with its endogenous promoter. To simplify subsequent subcloning steps the MUC26up primer was designed to contain Smal cutting site. The amplification reaction was performed using SafeFail PCR amplification kit (Epicentre). The resulting 2.6 kb product was purified using agarose gel electrophoresis (Current Protocols in Molecular Biology, Unit 2A Agarose gel electrophoresis). Briefly, the sample was loaded onto a 0.8% agarose gel and run in TAE buffer at 50 V for 1 hour. The gel was stained using ethidium bromide (5 ng/mL for 30 minutes) and the DNA band visualized on transluminator at 2500 W/cm2. An agar plug containing the 2.6 kb amplification product was excised. The DNA was purified from the agar gel using QIAquick kit (QIAGEN). To obtain the mucAB expression cassette as Smal fragment the PCR product was digested with Smal (NEB). The reaction yielded two fragments: 1.9 kb containing mucAB, and 0.7 kb representing sequence adjacent to mucAB on the 3'end. The 1.9 kb fragment was isolated using agarose gel electrophoresis and ligated into the Smal site in Puc19 using Rapid DNA ligation Kit (Roche). The transformation of E. coli cells (UltraMax™ DH5α-FT™ Competent cells, Life Technologies) yielded ampicillin resistant colonies carrying plasmid named pUCmuc that was used as source of mucAB expression cassette. The final step included the insertion of mucAB into pBRTNluxAM. The mucAB expression cassette was isolated from pUCmuc as Smal fragment and ligated into Pvull site of pBRTNluxAM. The final plasmid was named pBRTNluxAMmuc631 (FIG. 6).

The bioluminescent mucAB⁺ β-lac tester strain was created by transformation of TA1535 Salmonella strain with pBRTNluxAMmuc631. The new strain was named SA1535pBRTNluxAMmuc631. Since the mucAB protects Salmonella cells against killing by UV (see, for example, Walker, G. C., 1977), the UV cytotoxicity was used to confirm functionality of the cloned mucAB expression cassette. In this experiment the UV cytotoxicity for pBRTNluxAMmuc631 was compared with mucAB⁺ strain TA100 and mucAB⁻ strains TA1535 and SABRTN/uxAM (FIG. 7). As expected our new strain SA1535pBRTNluxAMmuc631 and mucAB⁺ TA100 showed almost identical resistance against killing by UV. In contrast, parental mucAB⁻ strains TA1535 and SABRTNluxAM were significantly more sensitive to UV effects. Those skilled in the art will appreciate that this data demonstrate the proper functionality of the mucAB expression cassette.

Detection of Mutagens Using Bioluminescent β-lac Assay

Bioluminescent β-lac assay utilized genetically modified β-lactamase supplied on plasmids pBRTNluxAM or pBRTNluxAMmuc631. In this assay, a reverse mutation event G to A restoring the wild type β-lactamase serves as an indicator for mutagenicity. The bioluminescence provided a simple tool for detection of revertants. In addition, each cell carries multiple targets for reverse mutation event (multiple copies of plasmids) and the ampicillin selection allows using full LB medium (Life Technologies). Thus, the assay can be performed with, e.g., <30%g of the test article, and provides suitable results, for example, in about 17–24 hrs.

A frozen aliquot of cells (500 µl; cell concentration OD=0.5, freezing medium LB supplemented with 10% DMSO) was inoculated into 35 mL of LB medium supplemented with 50 µg/mL kanamycin. The culture was grown at 30° C. for 15–18 hr (overnight) under agitation of 250 rpm. The overnight culture was diluted 3:1 with fresh kanamycin supplemented LB medium and grown at 37° C. until the cell density reached $OD_{600}$=0.5–0.6 (approximately 1–2 hr). Then, cells were washed in fresh NB medium and the final cell density was adjusted to $OD_{600}$=0.65. The cells were exposed in the liquid medium consisting of 2.2 µl PBS or S9 suspension, 9 µl cell suspension and 1.25 µl tested compound or DMSO. The mix was incubated in V-bottom shaped 96 well plates at 37° C. for 4 hours. A top agar mix containing 1.0% Bactoagar, 0.5% NaCl) was prepared and then kept at 50° C. Twenty five µl of the top agar was added to the treatment culture and plated on the 96-well plates where each well contained 150 µl LB agar supplemented with 300 µg/mL ampicillin and 40 µg/mL kanamycin. Plates were incubated at 37° C. for 16–18 hours. Luminescent microcolonies of revertants were visualized using photon counting CCD camera (Lumi-Imager, Boehringer). The increase in numbers of luminescent microcolonies in treated wells versus untreated wells indicated mutagenicity of tested compound (FIG. 8).

Although the assays of the present invention can be used to detect chemical mutagenicity, it could be also applied for evaluation of environmental genotoxicants including, for example, radioactivity (X-rays), magnetic fields, and the like.

LITERATURE

Ames, B. N. "The detection of chemical mutagens with enteric bacteria," In *Chemical Mutagens: Principles and Methods for Their Detection*, A. Hollaender, ed., Plenum, N.Y., 1: 267–282 (1971);

Ames, B. N., "Carcinogens are mutagens: their detection and classification," *Environ. Health Perspect.* 6: 115–118 (1973);

Ames, B. N. et al., "Carcinogens are mutagens: a simple test system combining liver homogenates for activation and bacteria for detection," *Proc. Natl. Acad. Sci. USA* 70: 2281–2285 (1973a)(co-incubation of a carcinogen, a rat or human liver homogenate, and the bacterial tester strain on a petri plate);

Ames, B. N. et al., "An improved bacterial test system for the detection and classification of mutagens and carcinogens," *Proc. Natl. Acad. Sci. USA* 70: 782–786 (1973b);

Ames, B. N. et al., Methods for detecting carcinogens and mutagens with *Salmonella*/mammalian-microsome mutagenicity test, *Mutation Res.* 31: 347–364 (1975);

Bosworth, D. et al., "A forward mutation assay using ampicillin-resistance in *Escherichia coli* designed for investigating the mutagenicity of biological samples," *Mutagenesis* 2 (6): 455–468 (1987);

Bronstein, I. et al., "REVIEW: Chemilumiescent and Bioluminescent Reporter Gene Assays," *Anal. Biochem.* 219:169–181 (1994);

Brooks, T. M., "The use of a streamlined bacterial mutagenicity assay, the MINISCREEN," *Mutagenesis* 10(5): 447–448 (1995);

Burke, D. A. et al., "Use of the Miniscreen assay to screen novel compounds for bacterial mutagenicity in the pharmaceutical industry," *Mutagenesis* 11(2): 201–205(1996);

Chatterjee, J. & Meighen, E. A., "Biotechnological applications of bacterial bioluminescence (lux) genes," *Photochemistry and Photobiology* 62(4): 641–650 (1995);

Couse, N. L. & King, J. W., "Quantitation of the spiral plating technique for use with the *Salmonella*/mammalian microsome assay," *Environ. Mutagen.* 4:445–455 (1982);

DeFlora, S., "A 'Spiral Test' applied to bacterial mutagenesis assays," *Mutation Res.* 82: 213–227 (1981);

Delaire, M. et al., "Site-directed mutagenesis on TEM-1 β-lactamase: role of Glu166 in catalysis and substrate binding," Protein Engineering 4 (7): 805–810 (1991);

de Lorenzo, V., et al., "Mini-Tn5 transposon derivatives for insertion mutagenesis, promoter probing, and chromosomal insertion of cloned DNA in gram-negative eubacteria," *J. Bacteriol.* 172 (11): 6568–65 (1990);

de Lorenzo, V., et al., "Engineering of alkyl- and haloaromatic-responsive gene expression with mini-transposons containing regulated promoters of biodegradative pathways of *Pseudomonas*," *Gene* 130 (1): 41–46 (1993);

Dunkel, V. C. et al., "Reproducibility of microbial mutagenicity assays: 1. Tests with *Salmonella typhimurium* and *Escherichia coli* using a standardized protocol," Environ. Mutagen. 6 (Suppl. 2): 1–25 (1984);

Dunkel, V. C. et al., "Reproducibility of microbial mutagenicity assays 11. Testing of carcinogens and noncarcinogens in *Salmonella typhimurium* and *Escherichia coli*," *Environ. Mutagen.* 7 (Suppl. 5): 1–248 (1985);

Falck, K., et al., "Mutascreen™, an automated bacterial mutagenicity assay," *Mutation Res.* 150:119–125 (1985);

Foster, P. L. et al., "Creation of a test Plasmid for Detecting G. C-to-T. A Transversions by Changing Serine to Arginine in the Active Site of β-Lactamase," *J. Bacteriol.* 169(6): 2476–2481 (1987);

Frackman, S. et al., "Cloning, organization, and expression of the bioluminescence genes of *Xenorhabdus luminescens*," *J. Bacteriol.* 172(10): 5767–5773 (1990);

Gatehouse, D. G. & Delow, G. F., "The development of a 'Microtitre' fluctuation test for the detection of indirect mutagens, and its use in the evaluation of mixed enzyme induction of the liver," *Mutation Res.* 60: 239–252 (1979);

Gee, P. et al., "Detection and classification of mutagens: A base set of base-specific *Salmonella* tester strains," *Proc. Natl. Acad. Sci. USA* 91: 11606–11610 (1994);

Green, M. H. L. et al., "Use of a simplified fluctuation test to detect low levels of mutagens," *Mutation Res.* 38: 33–42 (1976);

Green, M. H. L. & Muriel, W. J., "Mutagen testing using Trp⁻ reversion in *Escherichia coli*," *Mutation Res.* 38: 3–32 (1976);

Haworth, S., et al., "*Salmonella* mutagenicity results for 250 chemicals," *Environ. Mutagen.* 5(Suppl. 1): 3–142 (1983);

Hill, P. J., et al., "REVIEW: The application of lux genes," *Biotechnol. Appl. Biochem.* 17:3–14 (1993);

Hill, P. J. & Stewart, G. S. A. B, "Use of Lux Genes in Applied Biochemistry," *J. Biolumin. Chemilumin.* 9: 211–215 (1994);

Houk, V. S. et al., "Development and validation of the spiral *Salmonella* assay: An automated approach to bacterial mutagenicity testing," *Mutation Res.* 223: 49–64 (1989) (dose-response data is generated from a continuous concentration gradient on a single agar plate);

Houk, V. S. et al., "Use of the spiral *Salmonella* assay to detect the mutagenicity of complex mixtures," *Environ. Mol. Mutagen.* 17: 112–121 (1991);

Hour, T -C. et al., "A new mutagenicity assay method for frameshift mutagens based on deleting or inserting a guanosine nucleotide in the β-lactamase gene," *Mutagenesis* 10 (5): 433–438 (1995);

Jassim, S. A. A. et al., "In vivo Bioluminescence: A Cellular Reporter for Research and Industry," *J. Biolumin. Chemilumin.* 5:115–122 (1990);

Johnston, T. C. et al., "The nucleotide sequence of the luxA and luxB genes of *Xenorhabdus luminescens* HM and a comparison of the amino acid sequences of luciferases from four species of bioluminescent bacteria," *BBRC* 170: 407–415 (1990);

Kado, N. Y. et al., "A simple modification of the *Salmonella* liquid incubation assay: Increased sensitivity for detecting mutagens in human urine," *Mutat. Res.* 112:25–32 (1983);

Kato, H. et al., "Automation of the Ames test," in JEMS Abstract 31, published in *Mutation Res.* 334: 399 (1995);

Kier, L. E. et al., "The *Salmonella typhimurium*/ mammalian microsomal assay: A report of the U.S. Environmental Protection Agency Gene-Tox Program," *Mutation Res.* 168: 69–240 (1986);

Lee, C -C. et al., "A reverse mutagenicity assay for alkylating agents based on a point mutation in the β-lactamase gene at the active site serine codon," *Mutagenesis* 9 (5): 401–405 (1994);

Marines, F. & White, D. W. R., "Immobilization of *Escherichia coli* Expressing the lux Genes of *Xenorhabdus luminescens,*" *Appl. Environ. Microbiol.* 60(10): 3862–3863 (1994);

Maron, D. M. and Ames, B. N., "Revised methods for the *Salmonella* mutagenicity test," *Mutation Res.* 113: 173–215 (1983);

McCalla, D. R. and Voutsinos, D., "On the mutagenicity of nitrofurans," *Mutation. Res.* 26: 3–16 (1974);

McCalla, D. R. et al., "Mutagen screening with bacteria: niridazole and nitrofurans," *Mutation Res.* 31(1): 31–37 (1975);

McCann, J. et al., "Detection of carcinogens as mutagens: bacterial tester strains with R factor plasmids," *Proc. Natl. Acad. Sci. USA* 72(3): 979–983 (1975);

McPherson, M. F. and Nestmann, E. R., "The SIMULTEST approach for testing mutagens in the *Salmonella* microtitre fluctuation assay," *Environ. Mol. Mutagen.* 16: 21–25 (1990);

Meighen, E. A., "Enzymes and genes from the lux operons of bioluminescent bacteria," *Ann. Rev. Microbiol.* 42: 151–176 (1988);

Meighen, E. A., "Bacterial bioluminescence: organization, regulation, and application of the lux genes," *FASEB J.* 7:1016–1022 (1993);

Prival, M. J. and Mitchell, V. D, "Analysis of method for testing azo dyes for mutagenic activity in *Salmonella typhimurium* in the presence of flavin mononucleotide and hamster liver S-9," *Mutat. Res.* 97:103–116 (1982);

Reid, T. M., Morton, K. C., Wang, C. Y., and King, C. M., "Mutagenesis of azo dyes following metabolism by different reductive/oxidative systems," *Environ. Mutagen.* 6:247–259 (1984);

Sambrook, J., et al., Molecular Cloning: A Laboratory Manual, $2^{nd}$ ed., CSH Laboratory Press, Cold Spring Harbor, N.Y. (1989);

Schiesti, R. H., "Nonmutagenic carcinogens induce intrachromosomal recombination in yeast," *Nature* 337(6204): 285–288 (1989);

Silcock, D. J. et al., "Detection of a single genetically modified bacteial cell in soil by using charge coupled device enhanced microscopy," *Appl Environ. Microbiol.* 58: 2444–2448 (1992);

Skulachev, V. P., "The sodium cycle: a novel type of bacterial energetics," *J. Bioenerg. Biomembr.* 21(6): 635–647 (1989);

Stewart, G. S. A. B., "In vivo bioluminescence: new potentials for microbiology," *Letters in Appl. Microbiol.* 10: 1–8 (1990);

Stewart, G. S. A. B. & Williams, P., "lux genes and the applications of bacterial bioluminescence," *Journal of General Microbiology* 138: 1289–1300 (1992);

Surette, M. G. and Bassler, B. L., "Quorum sensing in *Escherichia coli* and *Salmonella typhimurium,*" *Proc. Natl. Acad. Sci. USA,* 95(12): 7046–7050 (1998);

Szittner, R. & Meighen, "Nucleotide sequence, expression and properties of luciferase coded by lux genes from a terrestrial bacterium," *JBC* 265: 16581–16587 (1990);

Van der Sand, S. T. et al., "Optimization of a lux gene expression in *Saccharomyces cerevisiae* as a tool to study gene regulation and plasmid segregation," *J. Bioluminescence and Chemiluminescence* 7: 220 (1992);

Voisey, C. R. & Marincs, F., "Elimination of Internal Restriction Enzyme Sites from a Bacterial Luminescence (luxCDABE) Operon," *BioTechniques* 24:56–58 (1998);

Vollmar, J. and Edler, L., "Tabular overview of statistical methods proposed for the analysis of Ames *Salmonella* assay data" In *Lecture Notes in Medical Informatics, Statistical Methods in Toxicology* (L. Hothorn, ed., Springer-Verlag, Berlin): 42–48 (1990);

Waleh, N. S., et al., "Development of a toxicity test to be coupled to the Ames *Salmonella* assay and the method of construction of the required strains," *Mutat Res.* 97:247–256 (1982);

Walker, G. C., "Plasmid (pKM101)-mediated enhancement of repair and mutagenesis: dependence on chromsomal genes in *Escherichia coli* K-12," *Mol. Gen. Genet* 152(1): 93–103 (1977);

Wilcox, P. et al., "Comparison of *Salmonella typhimurium* TA102 with *Escherichia coli* WP2 tester strains," *Mutagenesis* 5: 285–291 (1990);

Winson, M. K., et al., "Engineering the luxCDABE genes from *Photorhabdus luminescens* to provide a bioluminescent reporter for constitutive and promoter probe plasmids and mini-Tn5 constructs," *FEMS Microbiol. Lett.* 163(2): 193-202 (1998);

Xi, L. et al., "Cloning and nucleotide sequences of lux genes and characterization of luciferase of *Xenorhabdus luminescens* from a human wound," *J. Bacteriol* 173: 1399–1405 (1991);

Yahagi, T. et al., "Mutagenicity of carcinogenic azo dyes and their derivatives," *Cancer Left.* 1:91–97 (1975); and Zeiger, E., "The *Salmonella* mutagenicity assay for identification of presumptive carcinogens," in the *Handbook of Carcinogen Testing* (H. A. Milman and E. K. Weisburger, eds., Noyes Publishers, Park Ridge, N. J.): 83–99 (1985).

What is claimed is:

1. A genetically modified cell comprising an expressible heterologous lux(CDABE) gene complex under the control of a constitutive promoter, and, a reversible point mutation of a gene wherein said gene is a β-lactamase gene.

2. A cell as defined in claim 1 wherein said point mutation in said β-lactamase is in the active site serine codon and wherein said cell is selected from *Salmonella typhimurium* TA2220lux (UC25450) and *Salmonella tyhimurium* TA2211lux(UC2451).

* * * * *